(12) United States Patent
Hamano et al.

(10) Patent No.: US 6,309,653 B1
(45) Date of Patent: *Oct. 30, 2001

(54) CHOLESTEROL ESTER CLATHRATE, WATER-HOLDING COMPOSITION, HYDROUS COMPOSITIONS, COSMETICS CONTAINING THE SAME, AND PROCESS FOR THE PREPARATION THEREOF

(75) Inventors: Yohei Hamano; Akio Nasu; Takashi Minami; Takayuki Miyazaki; Noriko Tomita; Takashi Matsumoto; Yoshikazu Soyama, all of Kanagawa; Kenzo Ito, Shizuoka; Hajime Matsuda, Kanagawa; Hideyuki Sumiyoshi, Shizuoka, all of (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/229,840

(22) Filed: Jan. 11, 1999

Related U.S. Application Data

(63) Continuation-in-part of application No. 08/793,633, filed as application No. PCT/JP96/01815 on Jul. 1, 1996, now Pat. No. 5,871,759.

(30) Foreign Application Priority Data

Jun. 29, 1995 (JP) .................................................... 7-186154
Nov. 30, 1995 (JP) .................................................... 7-337870

(51) Int. Cl.$^7$ ............................... A61K 7/00; A61K 7/027
(52) U.S. Cl. ........................... 424/401; 424/64; 514/844; 514/845; 514/846; 514/847; 514/848; 514/169; 514/58

(58) Field of Search ............ 424/401, 64; 514/844–848, 514/58, 169

(56) References Cited

U.S. PATENT DOCUMENTS

| 5,194,250 | * | 3/1993 | Fairhurst | 424/70 |
| 5,447,920 | * | 9/1995 | Matsuda et al. | 514/58 |

FOREIGN PATENT DOCUMENTS

| 58-58139 (A) | 4/1983 | (JP) | B01F/17/52 |
| 63-194726 (A) | 8/1988 | (JP) | B01J/13/00 |
| 3-284611 (A) | 12/1991 | (JP) | A61K/7/00 |

* cited by examiner

Primary Examiner—Gollamudi S. Kishore
(74) Attorney, Agent, or Firm—Snider & Associates; Ronald R. Snider

(57) ABSTRACT

A cholesterol ester clathrate comprising a cholesterol ester included in a hydroxyalkylated cyclodextrin; a hydrous composition comprising a hydroxyalkylated cyclodextrin, a cholesterol ester and water; a hydrous composition comprising a hydroxyalkylated cyclodextrin, a cholesterol ester, a hydrous stabilizer, and water; a hydrous composition comprising a hydroxyalkylated cyclodextrin, a cholesterol ester, a clay mineral, and water; cosmetics containing these hydrous compositions; and process for the preparation thereof. The clathrate exhibits an emulsifying effect in itself. Further, the hydrous compositions are excellent in water-holding capacity and are improved in hydration properties and separation stability at a high temperature.

32 Claims, 21 Drawing Sheets

(9 of 21 Drawing Sheet(s) Filed in Color)

EXAMPLE 1-1(x150)

COMP. EX. 1-1(x150)   100μm

EXAMPLE 1-1(x750)

COMP. EX. 1-1(x750)  20μm

EXAMPLE 1-1

COMP. EX. 1-1

EXAMPLE 2-3 (x300)

COMP. EX. 2-5 (x300)

EXAMPLE 3-33 (x300)   10μm

EXAMPLE 3-34 (x300)   10μm

EXAMPLE 3-35 (x300)   10μm

EXAMPLE 3-35 (x300)   10μm

EXAMPLE 3-37 (x300)  10μm

EXAMPLE 3-39 (x300)  10μm (X150)  20μm (X150)  20μm

CHOLESTEROL ESTER CLATHRATE, WATER-HOLDING COMPOSITION, HYDROUS COMPOSITIONS, COSMETICS CONTAINING THE SAME, AND PROCESS FOR THE PREPARATION THEREOF

RELATED APPLICATION

The present invention is a continuation-in-part of U.S. patent application Ser. No. 08/793,633 filed on Feb. 27, 1997 (now U.S. Pat. No. 5,871,759, issued on Feb. 16, 1999) which is a 371 of PCT/JP96/01815, filed on Jul. 1, 1996 which is incorporated by reference.

The file of this patent contains at least one drawing executed in color. Copies of this patent with color drawing(s) will be provided by the Patent and Trademark Office upon request and payment of the necessary fee.

FIELD OF THE INVENTION

The present invention relates to cholesterol ester clathrate and hydrous composition comprising thereof and more particular, relates to the improvement of the stability in hydrating and emulsifying said hydrous composition.

BACKGROUND OF THE INVENTION

Water-holding in skin is an essential factor for keeping the skin in good condition. So, a lot of cosmetics and pharmaceutical preparations which intend the moisturizing are sold in the market, and a lot of humectants are developed. Among of these, a hydrous oily component, e.g., cholesterol ester which is excellent in hydration property and moisturizing property, are used in particularly cosmetics.

However, in case of compounding such a hydrous oily component which was included a lot of water to the cosmetics, it had some problems in stability, since water was separated at a high temperature or temperature change with the passage of time.

Therefore, for keeping the stability of the cosmetics which comprising oil and water, various surfactants has been used in separately or by combining two or more as an emulsifier.

However, ionic surfactants such as alkyl sulfate and higher fatty acid salt has an apprehension of skin irritation, in the case where they are used at high concentration. And in case of using nonionic surfactants such as polyoxyethylene type, it has a problem in solubility such that nonionic surfactants inactivate an antiseptic such as paraben.

In order to solve these problems, it has been developed techniques which uses cyclodextrin or its derivatives as an emulsifier. Namely, Japanese Unexamined Patent Publication No. Sho 58-58139 discloses the technique of emulsification by the specific process that cyclodextrin is used by combination with oil soluble surfactant. Also, Japanese Unexamined Patent Publication No. Sho 63-194726 discloses the technique which is used methylated β-cyclodextrin as an assistant emulsifier.

However, the problems such as skin irritation has not solved completely, since conventional surfactants are used by combining in these techniques.

In order to solve these problems, as for the example which is obtained the emulsion cosmetics without using any surfactant, the content in Japanese Unexamined Patent Publication No. Hei 3-284611 and U.S. Pat. No. 5,447,920 are listed. Japanese Unexamined Patent Publication No. Hei 3-284611 discloses a cosmetic comprising a hydroxyalkylated cyclodextrin, oil and water. U.S. Pat. No. 5,447,920 discloses a liquid or powdery cosmetic composition which comprises an inclusion product with a hydroxyalkylated cyclodextrin formulated therein. The cosmetic containing the hydroxyalkylated cyclodextrin is described as having improved product characteristics such as useability and stability, and effectively preventing skin roughening.

However, although hydroxyalkylated cyclodextrin demonstrates excellent solubility in hydrophilic solvents such as water, it does not do well in emulsion cosmetics primarily due to hydroxyalkylated cyclodextrin's lack of solubility in nonpolar group such as oils. In other words, a cosmetic containing hydroxyalkylated cyclodextrin displays insufficient water-holding capacity for keeping the moisture if the cosmetics contain substantial amount of oils (e.g., a water-in-oil type of cosmetics).

Thereupon, it has been developed the techniques used a hydroxyalkylated cyclodextrin which is effectively functioned to the composition as a hydrous stabilizer at the same time as an emulsifier.

However, in the water-holding of lipstick, and the like by using these techniques, the water-holding under the severe conditions such that is left for a long period of time and at 90° C. in the preparation time, is still insufficient. It sometimes occurs the aggregation of coloring agent and separate into a water phase and an oil phase or an emulsion phase, it is desired the further improvement.

SUMMARY OF THE INVENTION

In view of the above-mentioned problems of the prior art, the object of the present invention is to provide a cholesterol clathrate which has an excellent stability, safety and high water-holding capacity for keeping the moisture, and has an emulsifying effect in itself, and is to provide a hydrous composition which has an excellent stability, safety and high hydrous capacity for keeping the moisture, and has extremely excellent effect which is not separated even under the severe condition such as high temperature.

As the result of diligent studies of the inventors for attaining the above-mentioned object, it has been found that cholesterol ester clathrate comprising a cholesterol ester included in a hydroxyalkylated cyclodextrin can be functioned as an excellent emulsifier by hydrophilic nature of cyclodextrin and lipophilic nature of cholesterol ester. And, in case of compounding the composition which comprising said cholesterol clathrate and water into the cosmetics and the like, it also has been found that the cosmetics which is excellent in stability and safety, and has the specific property which is rich in water-holding capacity for keeping the moisture can be obtained. Further, it also has been found that the compositions which comprising a hydroxyalkylated cyclodextrin, water, and a hydrous stabilizer has extremely high hydration properties, and the compositions which comprising a hydroxyalkylated cyclodextrin, a cholesterol ester, water, and a clay mineral can be improved the separation stability at high temperature. Accordingly, the present invention has been accomplished.

Namely, in a first aspect of the present invention, there is provided a cholesterol ester clathrate comprising a cholesterol ester which is partly included in a hydroxyalkylated cyclodextrin primarily due to the combined hydrophilic characteristic of hydroxyalkylated cyclodextrin and lipophilic characteristic of cholesterol ester. Said cholesterol ester clathrate forms small, fine emulsion particles which can be uniformly distributed in emulsion cosmetics.

In a second aspect of the present invention, there is provided a hydrous composition comprising a hydroxyalkylated cyclodextrin, a cholesterol ester and water.

In said hydrous composition, preferably, the hydrous composition is composed of water and the cholesterol ester clathrate which is formed by the hydroxyalkylated cyclodextrin and the cholesterol ester, wherein said cholesterol ester is partly included in the hydroxyalkylated cyclodextrin primarily due to the combined hydrophilic characteristic of hydroxyalkylated cyclodextrin and lipophilic characteristic of cholesterol ester. Said cholesterol ester clathrate-containing hydrous composition forms small, fine emulsion particles which can be uniformly distributed in the emulsion cosmetics.

Also, in said hydrous composition, preferably, said composition comprises 5 to 30% by weight of the hydroxyalkylated cyclodextrin, 5 to 80% by weight of the cholesterol ester, and 5 to 60% by weight of water.

Further, in said hydrous composition, preferably, the ratio of the compounding amount of the hydroxyalkylated cyclodextrin and the cholesterol ester is existed within the range represented by the slant line of the triangular diagram shown in FIG. 1.

In a third aspect of the present invention, there is provided a hydrous composition comprising a hydroxyalkylated cyclodextrin, water, and one or more of a hydrous stabilizer which is/are selected from the group such as alkylated polysiloxane polyethyleneglycol copolymer, alkyl silicated anhydrous silicate, alkyl-modified silicone resin coated powder, glyceryl-modified silicone resin coated powder, dextrin fatty acid ester.

In said hydrous composition, preferably, said hydrous composition further comprising a hydrous oily component.

Also, in said hydrous composition, preferably, said composition comprises 5 to 30% by weight of the hydroxyalkylated cyclodextrin, 5 to 60% by weight of water and 5 to 80% by weight of the hydrous oily component with respect to the whole amount of the hydrous composition.

Further, in said hydrous composition, preferably, the ratio of the compounding amount of the hydroxyalkylated cyclodextrin, water and the hydrous oily component is existed within the range represented by the slant line of the triangular diagram shown in FIG. 2.

In said hydrous composition, it is preferable to comprise 0.01 to 20% by weight of the hydrous stabilizer with respect to the whole amount of the hydrous composition.

Preferably, alkylated polysiloxane polyethyleneglycol copolymer is used as the hydrous stabilizer.

In a fourth aspect of the present invention, there is provided a hydrous composition which comprising a hydroxyalkylated cyclodextrin, a cholesterol ester, a clay mineral and water.

In said hydrous composition, preferably, said composition comprises 5 to 30% by weight of the hydroxyalkylated cyclodextrin, 5 to 80% by weight of the cholesterol ester, 0.01 to 20% by weight of the clay mineral, and 5 to 60% by weight of water with respect to the whole amount of the hydrous composition.

In said hydrous composition, preferably, the clay mineral is a swelling type clay mineral or an organophilic smectite, and in particular, synthetic sodium magnesium silicate is most preferable.

Further, in said hydrous composition, preferably, said composition further comprising hydrophobic silica.

In said hydrous composition, preferably, said composition comprises 0.01 to 20% by weight of hydrophobic silica with respect to the whole amount of the hydrous composition.

Also, in said hydrous composition, preferably, the ratio of the compounding amount of hydrophobic silica to the clay mineral is 2:1 to 1:4.

In a fifth aspect of the present invention, there is provided a cosmetics comprising a hydroxyalkylated cyclodextrin, a cholesterol ester and water.

In said cosmetics, preferably, a hydroxyalkylated cyclodextrin, a cholesterol ester and water are compounded as any one of said hydrous composition.

And, in said cosmetics, preferably, the emulsion type of the cosmetics is water-in-oil type.

Also, in said cosmetics, preferably, any one of said hydrous composition is compounded with 0.5 to 30% by weight with respect to the whole amount of the cosmetics.

In a sixth aspect of the present invention, there is provided a process for the preparation of a cholesterol ester clathrate which is obtained by stirring and mixing a hydroxyalkylated cyclodextrin and a cholesterol ester.

In a seventh aspect of the present invention, there is provided a process for the preparation of a hydrous composition which is obtained by stirring and mixing a hydroxyalkylated cyclodextrin, water, and, a cholesterol ester.

A process for the preparation of a hydrous composition which is obtained by stirring and mixing the cholesterol ester clathrate which is prepared by the process for the preparation of the hydrous composition, and water.

In said process for the preparation of the hydrous composition, preferably, 5 to 30% by weight of the hydroxyalkylated cyclodextrin, 5 to 80% by weight of the cholesterol ester, 5 to 60% by weight of water are compounded.

In said process for the preparation of the hydrous composition, preferably, the ratio of the compounding amount of the hydroxyalkylated cyclodextrin and the cholesterol ester is existed within the range represented by the slant line of the triangular diagram shown in FIG. 1.

In a eighth aspect of the present invention, there is provided a process for the preparation of the hydrous composition which is obtained by stirring and mixing a hydroxyalkylated cyclodextrin; water; one or more of a hydrous stabilizer which is/are selected from the group such as alkylated polysiloxane polyethyleneglycol copolymer, alkyl silicated anhydrous silicate, alkyl-modified silicone resin coated powder, glyceryl-modified silicone resin coated powder and dextrin fatty acid ester; and a hydrous oily component.

In said process for the preparation of the hydrous composition, preferably, 5 to 30% by weight of the hydroxyalkylated cyclodextrin, 5 to 60% by weight of water, and 5 to 80% by weight of the hydrous oily component are compounded with respect to the whole amount of the hydrous composition.

In said process for the preparation of the hydrous composition, preferably, the ratio of the compounding amount of the hydroxyalkylated cyclodextrin, water, and the hydrous oily component is existed within the range represented by the slant line of the triangular diagram shown in FIG. 1.

In said process for the preparation of the hydrous composition, preferably, 0.01 to 20% by weight of the hydrous stabilizer is compounded with respect to the whole amount of the hydrous composition.

Preferably, alkylated polysiloxane polyethyleneglycol copolymer is used as the hydrous stabilizer.

In a ninth aspect of the present invention, there is provided a process for the preparation of the hydrous composition which is obtained by stirring and mixing a hydroxyalkylated cyclodextrin, a cholesterol ester, a clay mineral, and water.

In said process for the preparation of the hydrous composition, preferably, 5 to 30% by weight of the hydroxy alkylated cyclodextrin, 5 to 80% by weight of the cholesterol ester, 0.01 to 20% by weight of the clay mineral, and 5 to 60% by weight of water are compounded with respect to the whole amount of the hydrous composition.

Also, in said process for the preparation of the hydrous composition, the clay mineral is a swelling type clay mineral or an organophilic smectite, and in particular, synthetic sodium magnesium silicate is most preferable.

Further, in said process for the preparation of the hydrous composition, preferably, the hydrous composition is obtained by compounding hydrophobic silica, and stirring and mixing it.

In said process for the preparation of the hydrous composition, preferably, 0.01 to 20% by weight of hydrophobic silica is compounded.

Also, in said process for the preparation of the hydrous composition, preferably, the ratio of the compounding amount of hydrophobic silica to the clay mineral is 2:1 to 1:4.

In a tenth aspect of the present invention, there is provided a process for the preparation of the cosmetics which is obtained by stirring and mixing the hydrous composition which is prepared by any one of said process for the preparation of the hydrous composition and other ingredients.

In said process for the preparation of the cosmetics, preferably, 0.5 to 30% by weight of the hydrous composition which is prepared by any one of said process for the preparation of the hydrous composition, is compounded with respect to the whole amount of the cosmetics.

In the following, the constitutions of the present invention will be explained in further detail.

CONSTITUENTS

Hydroxyalkylated Cyclodextrin

A hydroxyalkylated cyclodextrin (hereinafter, referred to as HACD) used in the present invention is the preparation which includes a hydroxyalkyl group into a hydroxyl group of cyclodextrin (hereinafter, referred to as CD) which is well known as cyclic oligosaccharide in conventional. Namely, the preparation includes the hydroxyalkyl group which has hydrophobic nature, into the hydroxyl group of CD, and thereby its hydrophobic nature is enlarged.

The CD is an oligosaccharide in which a glucose residue is linked cyclically by α-1, 4-linkage, and α-CD, β-CD, and γ-CD which is comprised of a glucose residue of 6, 7, and 8 respectively are known in general. In the present invention, one or more of these CD can use by selecting.

As for the hydroxyalkyl group which substitute for the hydroxyl group of CD, a hydroxyethyl group, a hydroxypropyl group and the like are mainly used. The HACD can be obtained by doing substitution reaction of these hydroxyalkyl groups and the hydroxyl group. Examples of the HACD include hydroxyethylated cyclodextrin, hydroxypropylated cyclodextrin, hydroxybutylated cyclodextrin, dihydroxypropylated cyclodextrin and the like.

The preferable degree of substitution of a hydroxyl group and a hydroxyalkyl group in the present invention is 1 to 14 per CD.

Among of these HACD, in considering the price, easiness of preparation, usability, and water solubility, hydroxyethyl β-CD or hydroxypropyl β-CD is preferable. However, the HACD of the present invention is not limited to these.

The process for the preparation of the HACD is known several process in conventional, it will be shown one example in the following.

Namely, dissolved 100 g of β-CD into 150 ml of 20% NaOH water solution, and gradually dropped 50 ml of propylene oxide under keeping at 30° C., and then the reaction was keeping under stirring 20 hours. After the end of the reaction, neutralized it pH 6.0 by hydrochloric acid and put it into permeable membrane tube, and then it was desalted under flowing water in 24 hours. After then, dry it by freezing drying machine, and about 90 g of hydroxypropyl β-CD was obtained. The degree of substitution of this hydroxypropyl β-CD per CD was 5.1.

Hydrous Oily Component

Examples of a hydrous oily component used in the present invention include a cholesterol ester.

Examples of the cholesterol ester as the hydrous oily component of the present invention include cholesterol and esters of higher fatty acid. As for the higher fatty acids, straight chain or branched chain fatty acid having a carbon number from 12 to 24 can be used, e.g., myristic acid, palmitic acid, palmitoleic acid, stearic acid, oleic acid, linoleic acid, linolenic acid, arachidic acid and the like are included. In the present invention, it is used by selecting from one or more of these higher fatty acids. As for the higher fatty acid which constitute the ester with cholesterol used in the present invention, stearic acid, oleic acid, palmitoleic acid, macadamia nut oil fatty acid are particularly preferable.

As for the cholesterol esters used in the present invention, cholesterol stearate, cholesterol oleate, cholesterol palmitate, cholesteryl ester of macadamia nut oil fatty acid are particularly preferable.

Hydrous Stabilizer

In the present invention, examples of a hydrous stabilizer include alkylated polysiloxane polyethyleneglycol copolymer, alkyl silicated anhydrous silicate, alkyl- modified silicone resin coated powder, glyceryl-modified silicone resin coated powder, dextrin fatty acid ester, and it is used by selecting one or more of these. All of these substances are low in both hydrophilic nature and lipophilic nature, it is thinkable that they may be existed on the boundary of water and oily component in membranous state. Among of these, in order to control the water evaporation rate in low, in particular, it is preferable to use alkylated polysiloxane polyethyleneglycol copolymer.

Clay Mineral

As for a clay mineral used in the present invention, a swelling type clay mineral and an organophilic smectite are exemplified. Examples of the swelling type clay mineral preferably used in the present invention include, e.g., synthetic sodium magnesium silicate, lithium teniorite, sodium tetra silicate mica, lithium hectorite, and the like. As compared with that a conventional non-swelling type clay mineral such as natural mica is not swelled, these swelling type clay minerals have hydrous swelling property that the clay mineral is swelled up in the case where water molecule is added to the middle of the crystal layer.

As for the organophilic smectite preferably used in the present invention, dimethyl stearyl ammonium hectorite, aluminium magnesium silicate processed with distearyldimethyl ammonium chloride, and the like are listed.

Among of these clay minerals, it is preferable to use particularly synthetic sodium magnesium silicate of the swelling type clay mineral, for the improvement of the separation stability at a high temperature.

HYDROUS COMPOSITION (1) Cholesterol Ester Clathrate and Hydrous Composition Comprising Thereof A cholesterol ester clathrate of the present invention is formed by stirring and mixing a HACD and a cholesterol ester.

A hydrous composition of the present invention comprising a cholesterol ester clathrate and water.

The hydrous composition can be obtained by stirring and mixing a cholesterol ester clathrate and water. In said hydrous composition, a cholesterol ester clathrate forms micelle constitution and holds the water content. Said hydrous composition also can be obtained by stirring and mixing a HACD, a cholesterol ester and water. FIG. 1 shows the triangular diagram of the result of water retention test, by using HP-β-CD as a HACD and cholesteryl ester of macadamia nut oil fatty acid as the cholesterol ester. In 1 and 2 of the triangular diagram, the composition is separated into two phases, and the favorable cholesterol ester clathrate cannot be obtained. On the other hand, in 3 to 6 of the triangular diagram, the compositions become creamlike wherein the emulsion particles are in homogeneity, and the stable hydrous compositions are obtained. Accordingly, as for the hydrous composition of the present invention, preferably, the ratio of the amount of HP-β-CD and cholesteryl ester of macadamia nut oil fatty acid is existed within the range which is represented by the slant line of FIG. 1.

(2) Hydrous Composition Comprising a Hydrous Stabilizer

A hydrous composition comprising a hydrous stabilizer of the present invention is composed of a HACD, water and a hydrous stabilizer, and further can be comprised of a hydrous oily component as additional ingredient.

In a hydrous composition of the present invention, preferably, 5 to 30% by weight of the HACD, 5 to 60% by weight of water, and 5 to 80% by weight of the hydrous oily component are compounded with respect to the whole amount of the hydrous composition. Further, preferably, the ratio of the compounding amount of the HACD, water, and the hydrous oily component is existed within the range of the triangular diagram shown in FIG. 2. In the case where the ratio of the compounding amount is not existed within the range, it is difficult to obtain the expected composition, since the separation is occurred in the middle of a water phase and an emulsion phase.

Said hydrous composition can be obtained by dispersing the hydrous stabilizer into the hydrous oily component, adding and stirring the HACD in water solution to this, and adding and further stirring the rest of water to it.

(3) Hydrous Composition Comprising a Clay Mineral

A hydrous composition comprising a clay mineral of the present invention is composed of a HACD, a cholesterol ester, a clay mineral, and water.

In a hydrous composition of the present invention, preferably, 5 to 30% by weight of the HACD, 5 to 80% by weight of the cholesterol ester, 0.01 to 20% by weight of the clay mineral, and 5 to 60% by weight of water are compounded with respect to the whole amount of the hydrous composition. In the case where the compounding amount is not within said range, the preferable emulsion phase cannot be formed. In the case where the compounding amount of the clay mineral is not within said range, the improvement of the separation stability at high temperature become insufficient.

Further, in the case where hydrophobic silica is compounded into said hydrous composition, by compounding just a small amount of the clay mineral, the hydrous composition which is improved the separation stability can be obtained. In particular, hydrophobic silica is preferably compounded within the range of 0.01 to 20% by weight, and the ratio of the compounding amount of hydrophobic silica to the clay mineral is preferably 2:1 to 1:4.

Said hydrous composition can be obtained by dispersing the clay mineral into the cholesterol ester and gradually adding and stirring the HACD in water solution to this, and adding and further stirring the rest of water.

And, said each hydrous composition, except for said essential and selected ingredients, can be compounded the ingredients e.g., oily components such as squalane; humectants such as glycerin; wax such as candelilla wax; high polymers such as polyglyceride; medicaments such as glycyrrhizinic acid; natural surfactants such as recinol, and the like.

COSMETICS COMPRISING A HYDROUS COMPOSITION

In the cosmetics of the present invention, it is possible to obtain the cosmetics which is rich in stability and safety, and is excellent in water-holding capacity, by compounding said various hydrous compositions. Also, the emulsion type of said hydrous composition is preferably water-in-oil type, and in particular, it is preferable to use said hydrous composition as a water-in-oil cosmetics.

In this case, it is necessary to compound the hydrous composition of the present invention within the degree that the effects of said hydrous composition are sufficiently exhibited. The preferable compounding amount of said hydrous composition is 0.5 to 30% by weight with respect to the whole amount of the cosmetics.

The cosmetics in accordance with the present invention are prepared by normal techniques except for compounding the various hydrous composition of the present invention which was prepared in advance.

The cosmetics in accordance with the present invention, in addition to the hydrous composition of the present invention, can be compounded the various ingredients which is normally used for cosmetics within the degree that the effects of said hydrous composition of the present invention are not spoiled. Examples of said various ingredients are listed fats and oils of natural animals and vegetables such as macadamia nut oil, evening primrose oil, castor oil, olive oil, mink oil, jojoba oil, lanolin, squalene and the like; wax such as liquid paraffin, paraffin wax, polyethylene wax, carnauba wax and the like; higher alcohols such as cetyl alcohol, isocetyl alcohol, stearyl alcohol, isostearyl alcohol and the like; higher fatty acids such as myristic acid, palmitic acid, stearic acid, behenic acid, isostearic acid and the like; esters such as isopropyl myristate, isopropyl palmitate, isopropyl isostearate, diisostearyl malate, trimethylolpropane triisostearate, glyceryl isostearate, neopentyl glycol dicaprate, glyceryl 2-ethylhexanoate, and the like; other oily components such as polar oils (e.g., diethylene glycol monopropylene pentaerythritol ether, ethyl linoleate, polyoxypropylene butyl ether, and the like), silicone oils and the like; soluble powder bases such as D-mannitol, lactose and the like; humectants such as glycerin, hyaluronic acid and the like; medicaments such as vitamin C, vitamin E and the like; antiphlogistic; UV-absorber; UV-screening agent; antioxidant; antiseptic; viscosity modifier; coloring matters; crude drugs; perfume ingredient; pigment, and the like.

The cosmetics in accordance with the present invention can be formed the configuration which corresponds to the various use application, e.g., creamlike, milky lotionlike, liquidlike, solidlike, sticklike, pencillike, and the like. In the case where the cosmetics are formed the configuration that is particular compounded a large amounts of oil phase ingredients such as wax of solidlike, sticklike, pencillike and the like, and that is almost never possessed water phase ingredients, the water-holding capacity of the cosmetics can be effectively exhibited.

As for the cosmetic which uses the hydrous composition of the present invention, the composition for lipstick comprising a large amounts of oil phase ingredients particular such as wax is preferable.

BRIEF DESCRIPTION OF THE DRAWINGS

The file of this patent contins at least one drawing executed in color. Copies of this patent with color drawing (s) will be provided by the Patent and Trademark Office upon request and payment of the necessary fee.

DETAILED DESCRIPTION OF THE PREFERRED EMBODIMENT

In the following, it will be explained the present invention in further detail?from the embodiments of the present invention. However, the present invention should not be limited to the following embodiments. Also, the compounding amount is expressed as parts by weight unless otherwise stated.

(1) Cholesterol Ester Clathrate and Hydrous Composition Comprising Thereof

In first, the inventors were studied about the physical properties of the cholesterol ester clathrate of the present invention. Namely, preparing the hydrous composition which comprising water and the cholesterol clathrate which included cholesteryl ester of macadamia nut oil fatty acid in hydroxypropyl β-CD (hereinafter referred to as HP-β-CD) under the following formulation. And, said composition was taken on the preparation and was observed by microscope.

The photographs and the results obtained by the microscope observation were shown in FIG. 3 and Table-1 respectively.

TABLE 1

|  | Example 1-1 | Comp. ex. 1-1 |
| --- | --- | --- |
| Ion-exchanged water | 40 | 40 |
| HP-β-CD | 10 | 0 |
| cholesteryl ester of macadamia nut oil fatty acid | 50 | 60 |
| Diameter of emulsion particle (μm) | 1 to 5 | 1 to 10 |
| Form of the composition | had a visco-crumbly | elasticity |

As is clear from the above-described results, the hydrous composition had a viscoelasticity, and its emulsion particle was small and also was formed nearly spherical in Example 1-1. On the other hand, in comparative example 1-1, the composition itself showed crumbly feeling and the emulsion particle was crooked shape and was big.

Figure 4A:
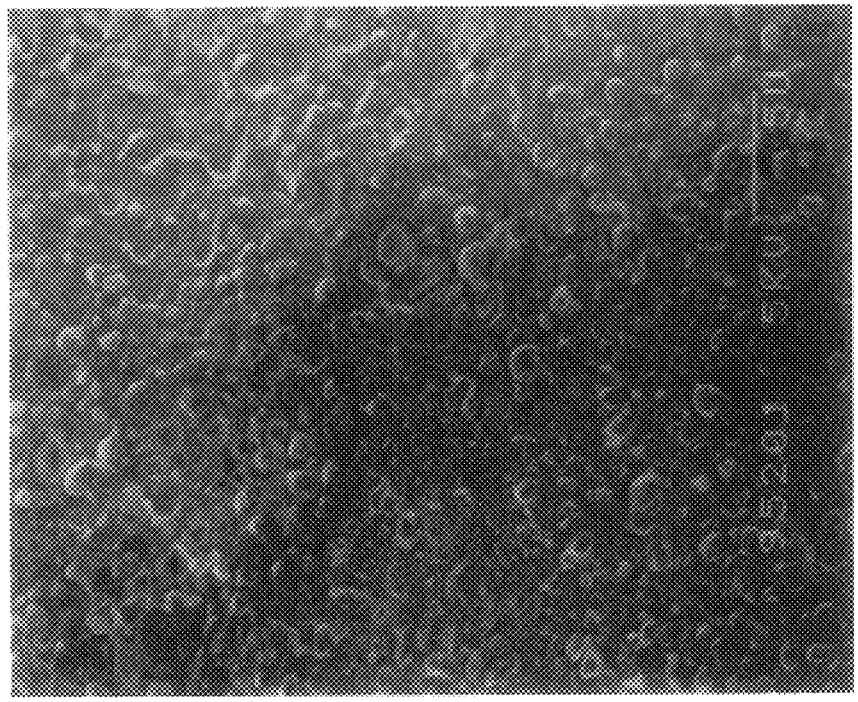
FIG. 4 are microphotographs which shows the hydration properties in the after case where Example 1-1 and Comparative example 1-1 were left for 24 hours.
Figure 4B:
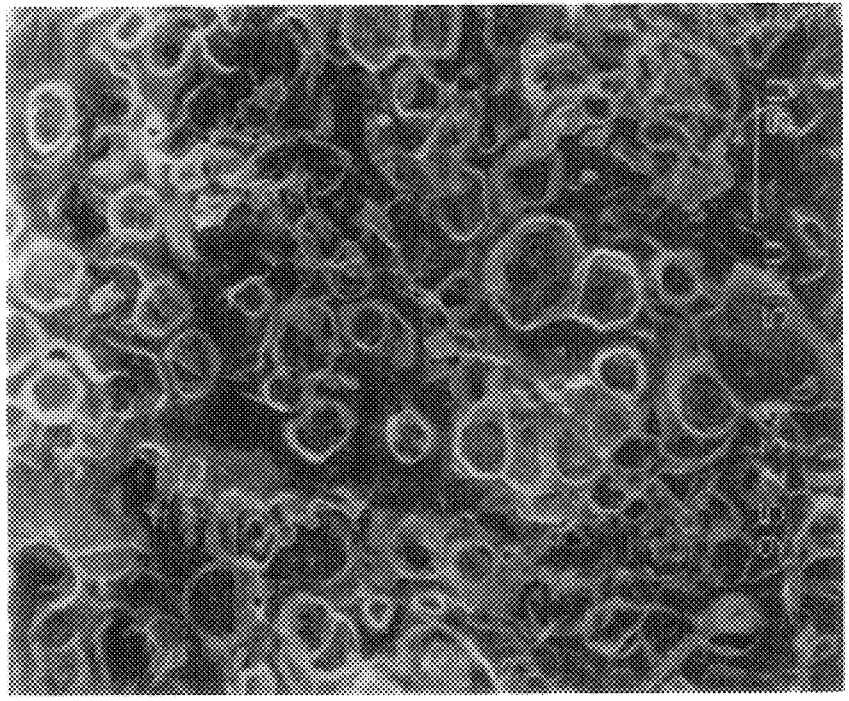

Further, the microphotographs of the composition in Example 1-1 and Comparative example 1-1 which were left for 24 hours, are shown in FIG. 4.

As is clear from the above-described results, in Comparative example 1-1, the diameter of emulsion particle became considerable big, so it cannot say that the emulsification was performed in stable. On the other hand, in Example 1-1, the diameter of emulsion particle was considerable small and the particle kept the state of spherical shape, so it can say that the emulsification was performed in stable.

Further, the inventors were performed the DSC measurement in Example 1-1 and Comparative example 1-1 under the following condition.

| [DSC Measurement] | |
| --- | --- |
| Measuring instrument | |
| measured by using Seiko Instruments Inc. DSC-100 | |
| Measuring condition | |
| Rate (Heating rate) | 5° C./min |
| Amount of the sample | 15.0 mg |
| Cell | Ag |
| Control cell | Al$_2$O$_3$ |
| Measured at the open condition | |
| Temperature range | RT to 150° C. |

Figure 5A:
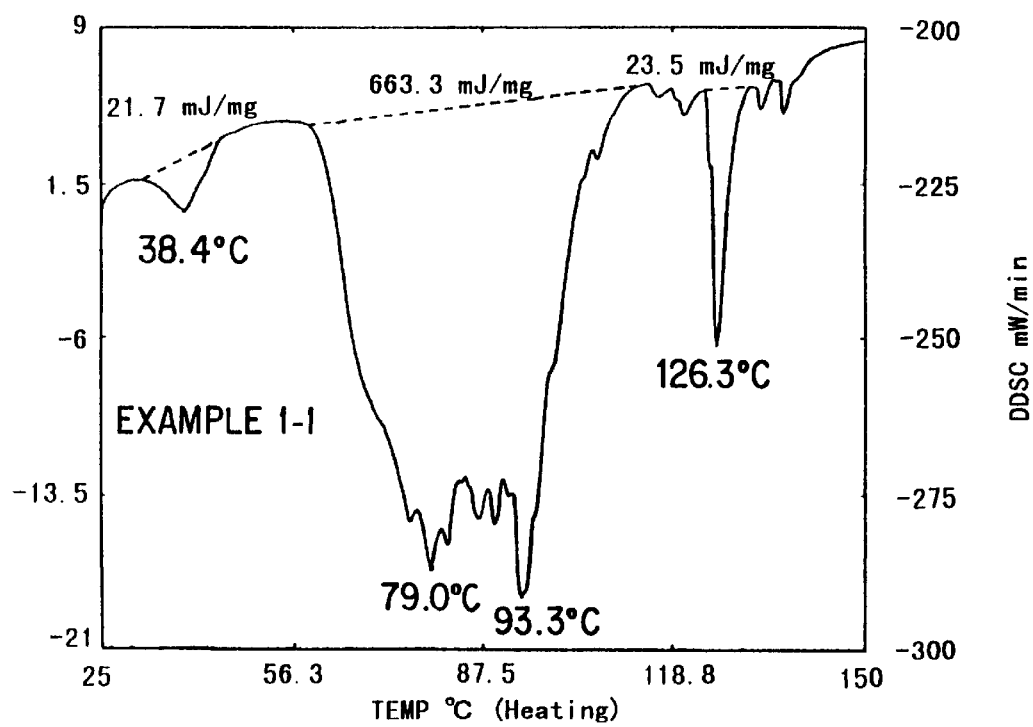
FIG. 5 are spectrum views of DSC measurement in Example 1-1 and Comparative example 1-1.
Figure 5B:
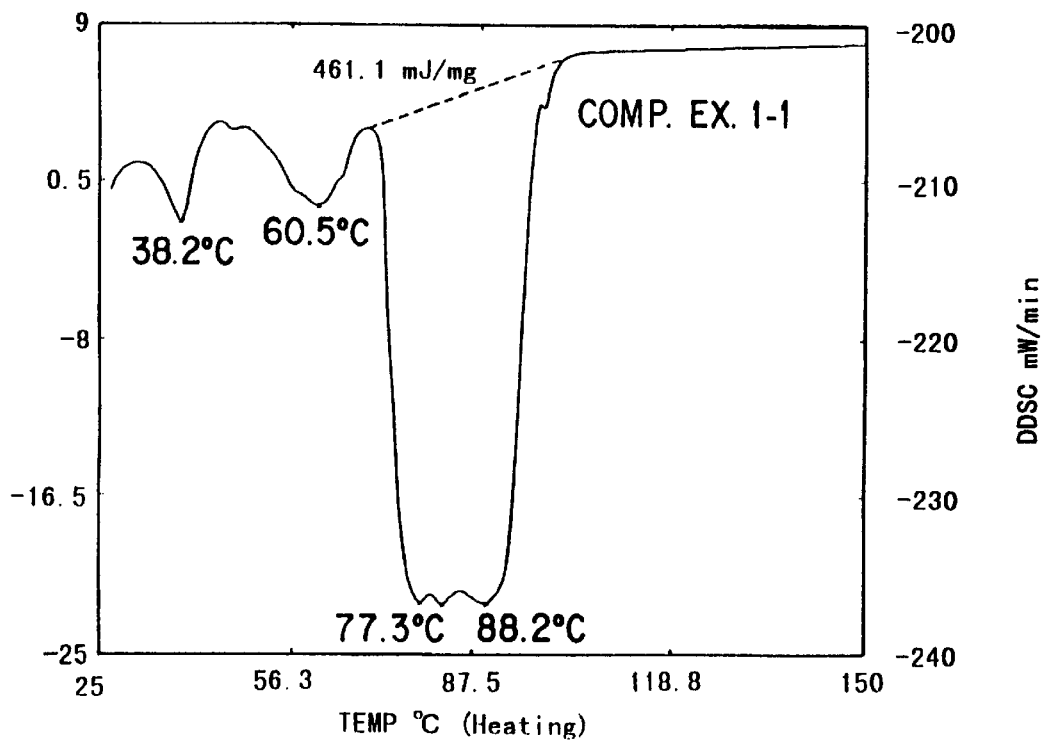

The results of DSC measurement are shown in FIG. 5.

In comparing the result of Example 1-1 with that of Comparative example 1-1, it was understood that the striking disparity was existed in the evaporation temperature of the water content. Namely, in the sample which removed HP-β-CD (Comparative example 1-1), the water evaporation peak can be observed at 65 to 90° C. However, in the sample which partly included the cholesterol ester in HP-β-CD (Example 1-1), the water evaporation peak can be observed at 79° C., 93.3° C., and 126.3° C., with the most significant peak shown at 126.3° C. So, it was suggested that the composition of the present invention (Example 1-1) possesses high water-holding capacity.

Accordingly, it was suggested that the hydrous composition of the present invention which comprising the cholesterol ester clathrate and water was excellent in water-holding capacity, and was also possible to attempt the emulsification in stable.

Figure 16A:
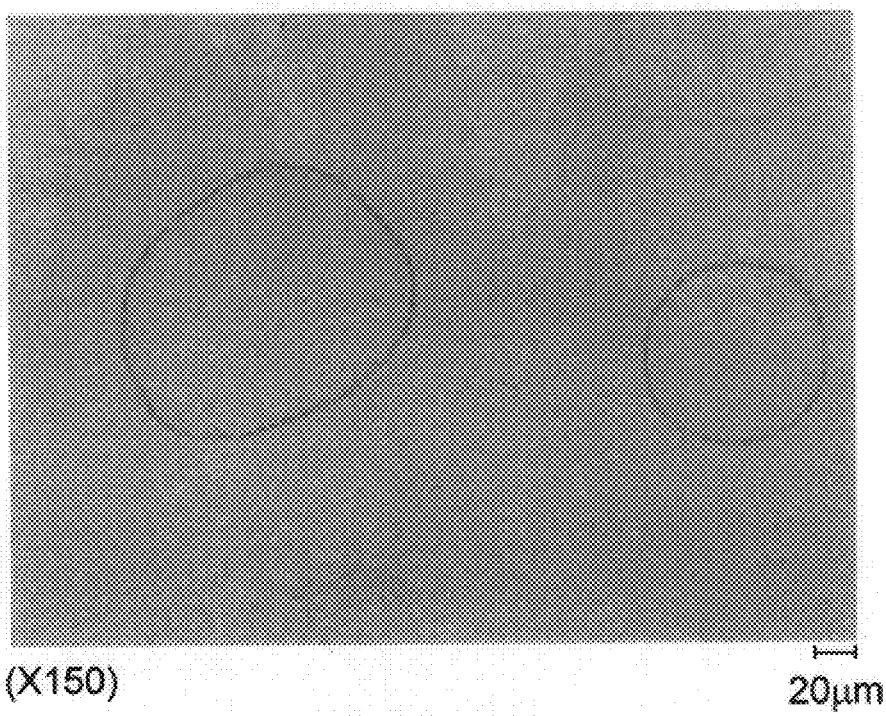
FIG. 16 displays a photograph showing two bottles containing differently prepared samples: left, a sample which contains hydroxyalkylated cyclodextrin stored overnight (this sample has the same characteristics as the product described in U.S. Pat. No. 5,447,920, issued to Matsuda et al.); right: a sample which contains the cholesterol ester clathrate hydrous composition stored overnight (this sample is the same as the Comparative Example 2-2 shown in Table 4). Both samples are water-in-oil type of emulsions.
Figure 16B:
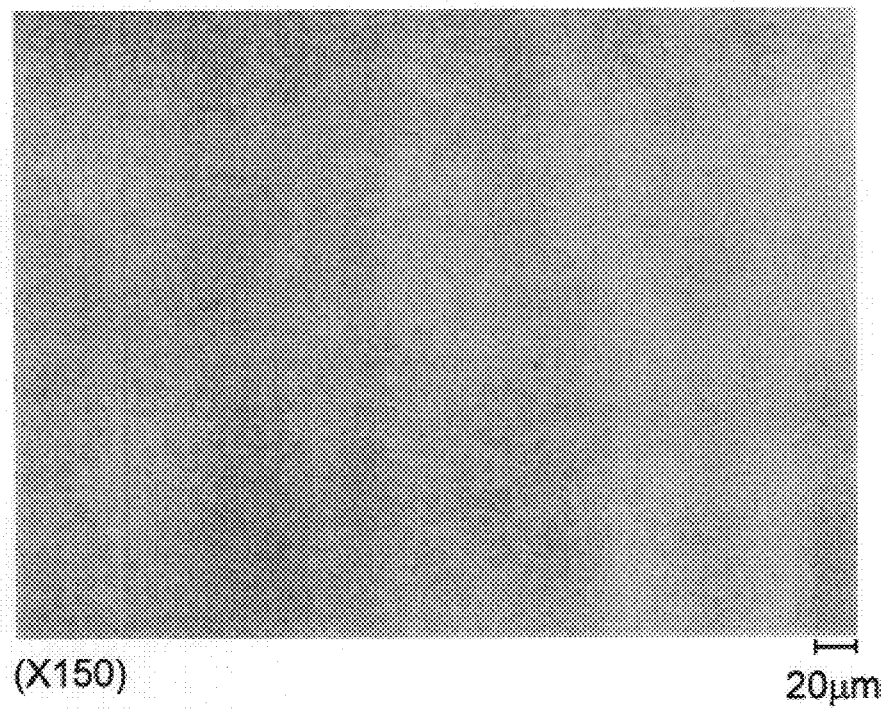
Figure 17:
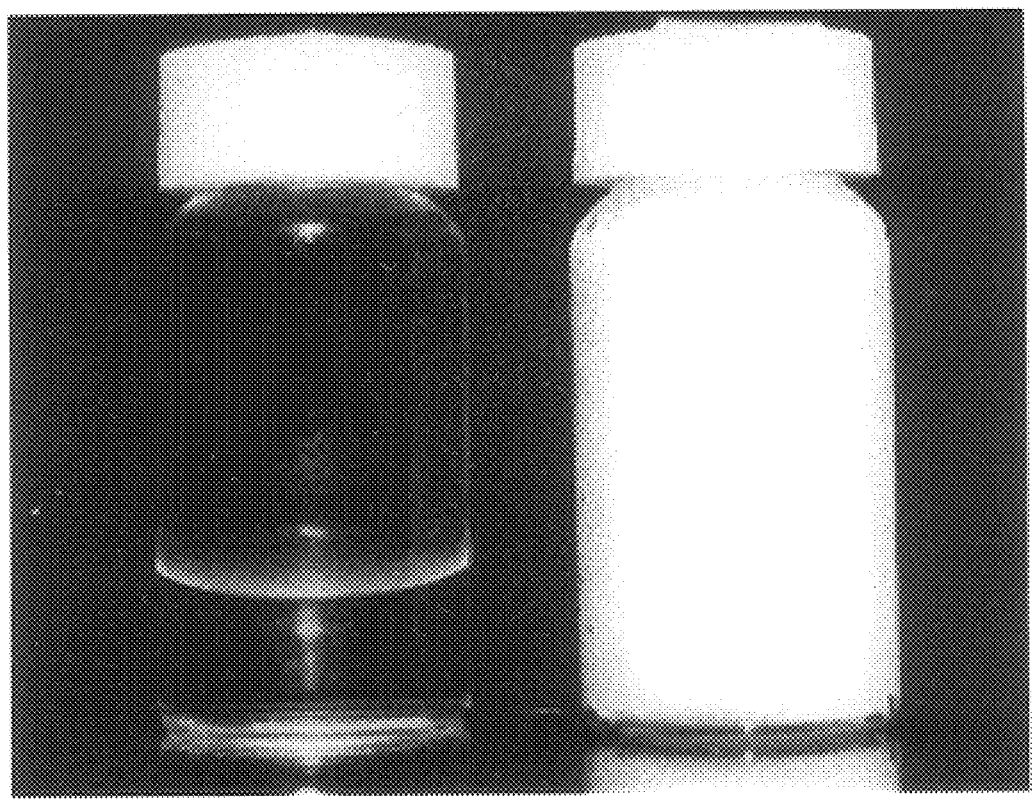
FIG. 17 shows two microphotographs (X150) of emulsion particles containing samples described in FIG. 16: left, emulsion particles taken from a sample containing hydroxyalkylated cyclodextrin (this sample has the same characteristics of the product described in U.S. Pat. No. 5,447,920, issued to Matsuda et al.); right: emulsion particles taken from a sample which contains the cholesterol ester clathrate hydrous composition (this sample is the same as the Comparative Example 2-2 shown in Table 4). Both samples are water-in-oil type of emulsions.
Figure 18:
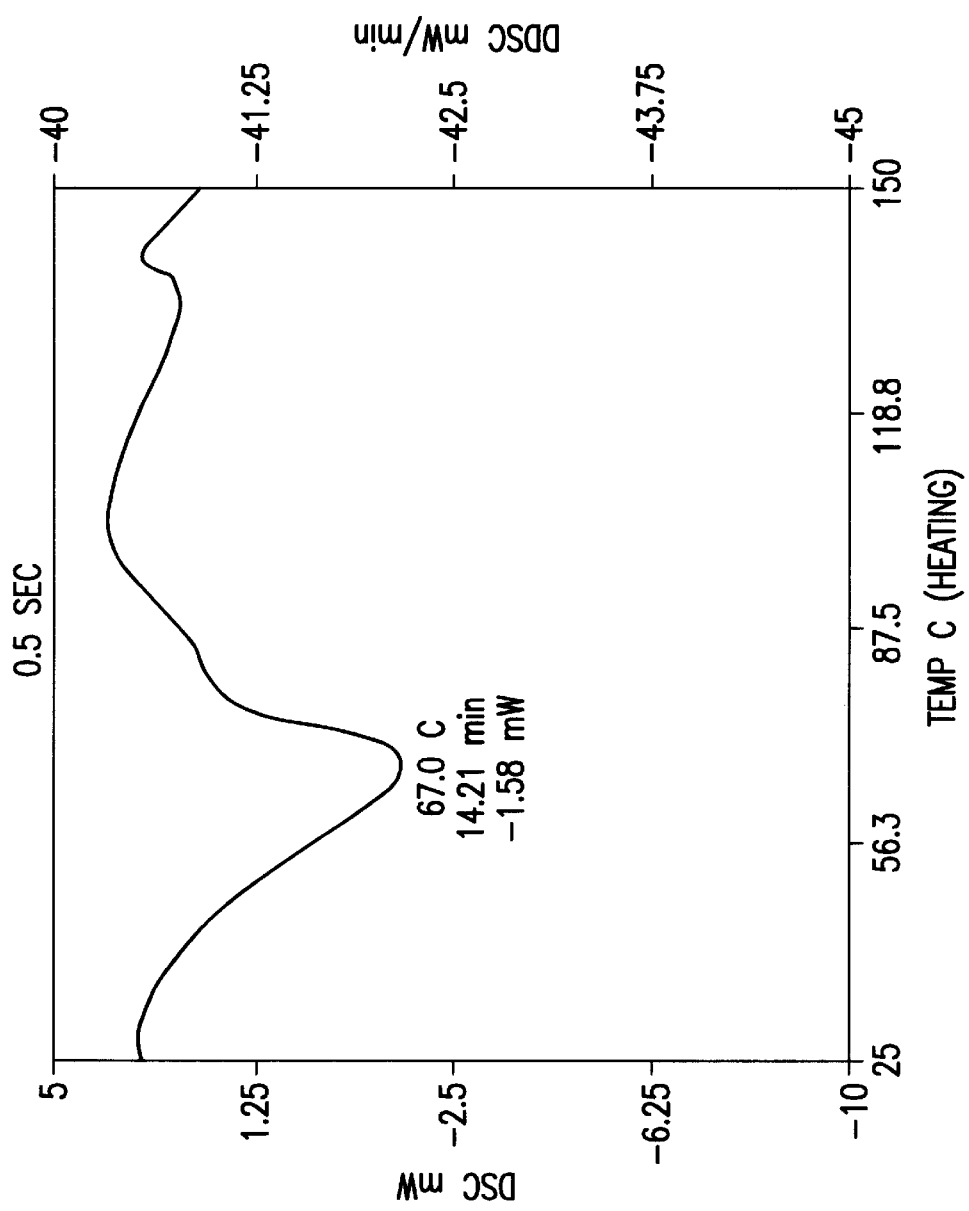
FIG. 18 shows the spectrum view of DSC measurement in a sample containing hydroxyalkylated cyclodextrin (which has the same characteristics as the product described in U.S. Pat. No. 5,447,920, issued to Matsuda et al.).

Comparative studies concerning the product disclosed in U.S. Pat. No. 5,447,920 issued to Matsuda et al. and that described in the present invention are conducted in the following manners: (1) testing the stability of the samples by letting the samples be stored at room temperature overnight (the results are shown in Table 1A and FIG. 16); (2) viewing the sizes of the emulsion particles by microscope after overnight storage (the results are shown in FIG. 17); and (3) measuring the evaporation temperature of the water content in Matsuda's sample (the result is shown in FIG. 18) by DSC measurement, which is used in comparison with the DSC measurement of Comparative Example 2-2 in FIG. 8 (i.e., Comparative Example 2-2 has the same composition as the cholesterol clathrate sample described in Table 1A and FIGS. 16 and 17 [see Table 4 for the composition of Comparative Example 2-2]).

TABLE 1A

| | Sample Containing Only HACD | Sample containing Cholesterol Ester Clathrate |
| --- | --- | --- |
| Perfume (Benzyl acetate) | 70 | — |
| YOFCO MAC* | — | 70 |
| Ion-exchange water | 20 | 20 |
| HP-β-CD | 10 | 10 |
| Diameter of Emulsion Particle (μm) | >20 | 1 or less |
| Emulsion state | Separated | Stable |

*YOFCO MAC: Trade name of cholesterol ester of macadamia nut oil fatty acid.

Table 1A shows a comparative study between the sample from Matsuda's U.S. Pat. No. 5,447,920 containing HACD and the sample containing cholesterol ester clathrate hydrous composition. Matsuda's sample was prepared by dissolving benzyl acetate (perfume), ion-exchange water, and HP-β-CD at 25° C. (because the perfume is volatile), followed by disper stirring for 10 minutes. The sample containing cholesterol ester clathrate hydrous composition was prepared by dissolving YOFCO MAC, ion exchange water, and HP-β-CD at 60° C., followed by disper stirring for 10 minutes. Both samples were then stored at room temperature overnight before further analysis.

As shown in Table 1, Matsuda's sample separated into two phases (the water phase and the oil phase), whereas the sample containing the cholesterol ester clathrate was still in homogeneous state. A photograph showing Matsuda's sample being separated into two phases (left) and the sample from the present invention being in homogeneous state (right) is exhibited in FIG. 16.

A drop of each of the samples taken from the above preparations was also viewed under the microscope. As shown in FIG. 17, Matsuda's sample (left) contains big (with diameter greater than 20 μm), well defined and well circumscribed inclusion body possibly due to HACD's lack of solubility in oil phase. On the other hand, the sample containing cholesterol ester clathrate comprises small, fine particles (with diameter less than 1 μm, as indicated in Table 1A) (right) which were homogeneously dispersed in the emulsion. No well defined and well circumscribed inclusion body was observed in the sample of the present invention, indicating that the fine particles created by the cholesterol ester clathrate are not inclusion bodies.

Figure 8A:
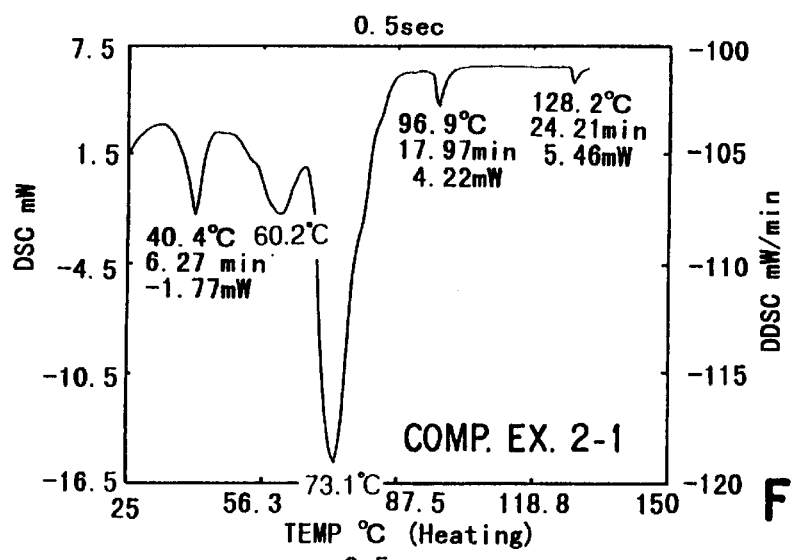
FIG. 8 are spectrum views of DSC measurement in Comparative example 2-1 to 2-3.
Figure 8B:
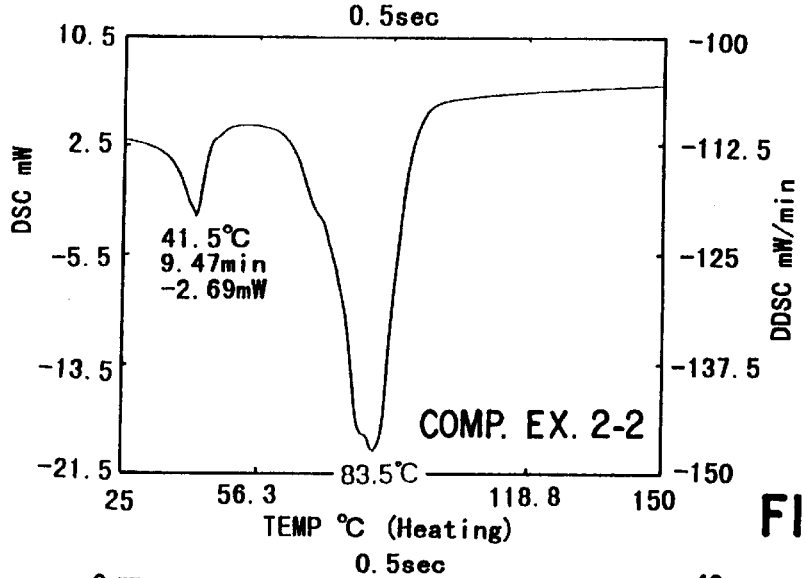
Figure 8C:
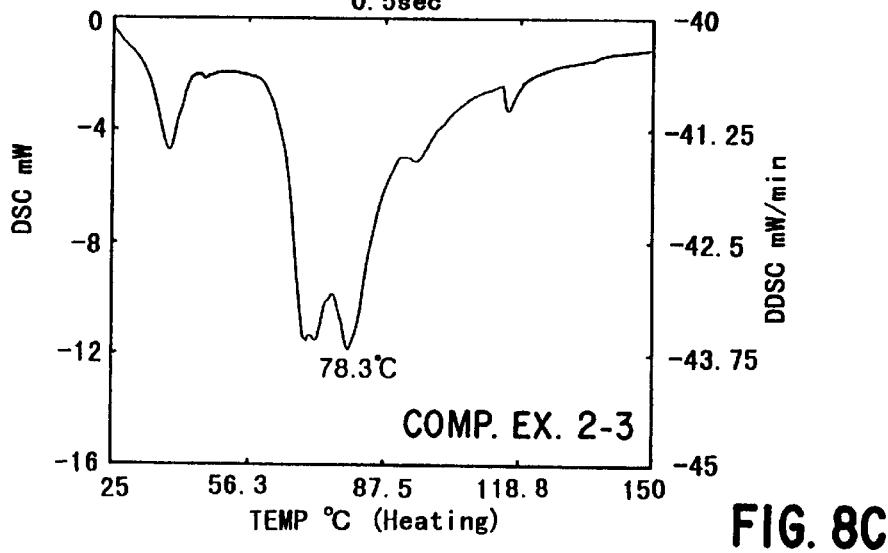

DSC measurement of Matsuda's sample shows that the water evaporation peak was at 67° C., which was contrary to the water evaporation peak at 83.5° C. of the sample containing the cholesterol ester clathrate hydrous composition (see Comparative Example 2-2 in FIG. 8). Additional studies of the water evaporation peak in samples containing cholesterol ester clathrate hydrous composition are also available (e.g., Example 1-1 has three evaporation peaks at 79° C., 93.3° C., and 126.3° C. [FIG. 5], Examples 2-1 and 2-2 has an evaporation peak at 106.4° C., Example 2-2 has an evaporation peak at 94.7° C. [FIG. 9], and Example 2-3 has two evaporation peaks at 104.4° C. and 120.4° C. [FIG. 12]). Because the higher the temperature where the water content is evaporated, the better the water content is preserved, it is therefore evident that the sample prepared in the present invention possesses higher water-holding capacity over Matsuda's sample.

Next, the inventors were studied about the effects in case of compounding the HACD.

The evaluation of emulsion stability has been done by the following standard.

[Emulsion Stability]

○: It was not observed the separation of the water phase and the oil phase even after kept the composition in 8 hours at 60° C.

Δ: It was observed the separation of the water phase and the emulsion phase in a part of the composition after kept the composition in 1 hour at 60° C.

x : It was observed the separation of the water phase and the oil phase or the emulsion phase after passed 1 hour at 60° C.

TABLE 2

| | Comp. ex. 1-2 | Example 1-2 | Example 1-3 | Example 1-4 |
|---|---|---|---|---|
| Cholesteryl ester of macadamia nut oil fatty acid | 50 | 50 | 50 | 50 |
| Ion-exchanged water | 40 | 40 | 40 | 40 |
| HE-β-CD | — | 10 | — | — |
| HP-β-CD | — | — | 10 | — |
| HB-β-CD | — | — | — | 10 |
| Diameter of emulsion particle (μm; 25° C.) | 1 to 10 | 1 to 5 | 1 to 5 | 1 to 8 |
| Form of the composition | crumbly | had a viscoelasticity | had a viscoelasticity | had a viscoelasticity |
| Diameter of emulsion particle (μm; 60° C.) | not existed | 1 to 5 | 1 to 5 | 1 to 8 |
| Emulsion stability (60° C.) | x | ○ | ○ | ○ |

As is clear from the above-described results, Comparative example 1-2 which was not compounded the HACD at all, was formed emulsion particle at 25° C. However, the emulsion stability at 60° C. was bad, emulsion particle was not formed, and the separation of the water phase and the oil phase was observed. On the other hand, all the Examples 1-2 to 1-4 which were compounded the HACD, were excellent in emulsion stability at 60° C., and also had a fine emulsion particle, and its form at 25° C. had a viscoelasticity. Example 1-2 and Example 1-3 which were compounded particularly HE-β-CD and HP-β-CD respectively, had further fine diameter of emulsion particle. So, it is preferable to use these as the HACD.

Accordingly, it is preferable to compound the HACD in the hydrous composition of the present invention.

Next, the inventors were compared the change of the water content of keratin by using the lipstick of the present invention which compounds the HACD, the cholesterol ester, and water (Example 1-5), the lipstick which compounds the hydrous composition comprising the cholesterol ester clathrate of the present invention and water (Example 1-6), the lipstick which was the same composition as these and was not comprising HP-β-CD and water (Comparative example 1-3).

These measurement condition is shown in the following:
[Measurement of The Water Content of Keratin]

After wiped off softly the water content of lip by tissue paper in a thermo-hygrostat room (22° C. and 45%), the conductance of the lip before putting lipstick on lip was measured. And then, putting lipstick on lip, and after passed 2 hours, wiped off the lipstick which was put on lip by tissue paper, and the conductance of the lip after put lipstick on lip was measured. And, the ratio of the conductance before put lipstick and the conductance after put lipstick were found.

TABLE 3

| | Comp. ex. 1-3 | Ex. 1-5 | Ex. 1-6 |
|---|---|---|---|
| Microcrystalline wax | 1.0 | 1.0 | 1.0 |
| Ceresin | 13.5 | 14.5 | 14.5 |
| Methylphenyl polysiloxane | 10.0 | 10.0 | 10.0 |
| Macadamia nut oil | 0.5 | 0.5 | 0.5 |
| Glyceryl triisostearate | 18.0 | 18.0 | 18.0 |
| Glyceryl tri(2-ethylhexanoate) | 30.67 | 17.03 | 19.66 |
| Lanolin | 5.0 | 5.0 | 5.0 |
| Adsorption refined lanolin | 5.0 | 5.0 | 5.0 |
| Cholesteryl ester of macadamia nut oil fatty acid | — | 5.0 | — |
| Dibasic calcium phosphate (anhydrous) | 1.0 | 1.0 | 1.0 |
| Dye | 0.25 | 0.25 | 0.25 |
| Coloring agent | 15.0 | 15.0 | 15.0 |
| Oxidation stabilizer | 0.04 | 0.04 | 0.04 |
| Perfume | 0.04 | 0.04 | 0.04 |
| Polyoxyethylene methylpolysiloxane copolymer | — | 0.5 | — |
| Synthetic sodium magnesium silicate | — | 2.0 | — |
| Ion-exchanged water | — | 4.0 | — |
| HP-β-CD | — | 1.0 | — |
| Calcium chloride dihydrate | — | 0.13 | — |
| Methyl polysiloxane emulsion | — | 0.01 | 0.01 |
| The hydrous composition of Example 1-1 | — | — | 10.0 |

Figure 6:
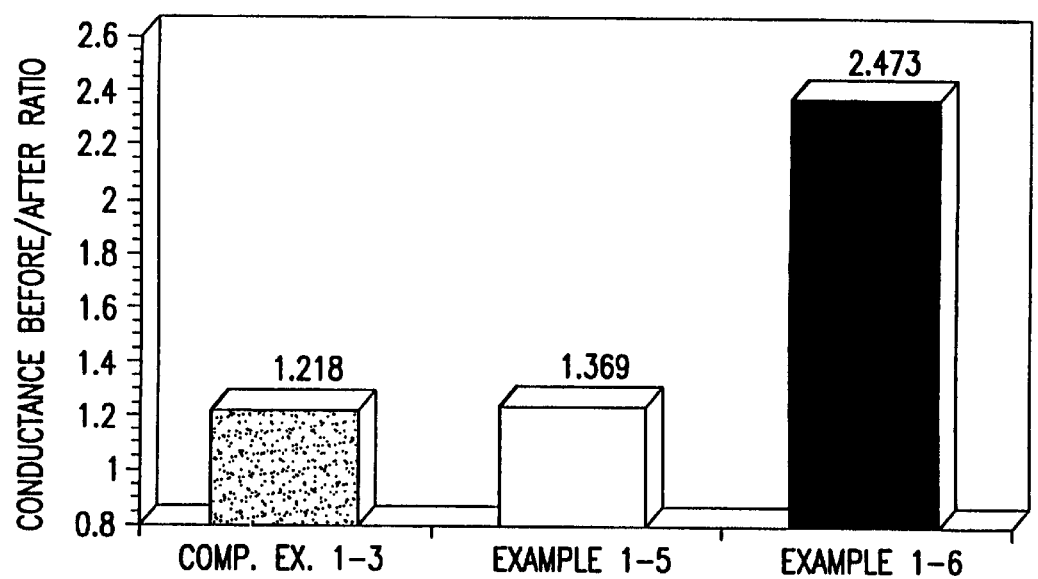
FIG. 6 is a chart comparing the water content of keratin in Example 1-5, Example 1-6, and Comparative example 1-3.

The measurement results of the water content of keratin in case of using the lipstick which was obtained by Example 1-5, Example 1-6, and Comparative example 1-3 are shown in FIG. 6.

As is clear from the drawing, in Example 1-5, it is suggested that the ratio of the conductance was slightly big as compared with the ratio of the conductance of Comparative example 1-3, and it can hold the more water content. Further, in Example 1-6, the ratio of the conductance was more than twice of the ratio of the conductance of Comparative example 1-3 and the sufficient water content was held.

And, when the evaluation of the usability was performed by the panel by using the lipsticks which were prepared by the above-mentioned formulation, Example 1-5 showed the characteristics such that was possessed the moisture feeling, was excellent in spreadability and affinity, and was less of stickiness as compared with Example 1-3.

Accordingly, in the case where the HACD, the cholesterol ester and water were compounded to the lipstick (Example 1-5), the lipstick which was slightly improved the water-holding capacity and was also excellent in usability, can be obtained. Further, before mixed with lipstick bases, the hydrous composition which comprising the cholesterol ester clathrate was prepared by the HACD, water, and the cholesterol ester. In the case where said hydrous composition was compounded to the lipstick (Example 1-6), the lipstick which had more than twice of water-holding capacity and was excellent in usability can be obtained. Accordingly, in the present invention, it is suggested that the moisture of the coated surface is keeping.

Further, the moisture effect was evaluated by measuring the penetrating amount of the water content, by using Example 1-6, Comparative example 1-3, and the lipstick which is used the conventional emulsion base as the same formulation with Example 1-6 in substitution of the hydrous composition of the present invention (Comparative example 1-4).

Figure 7:
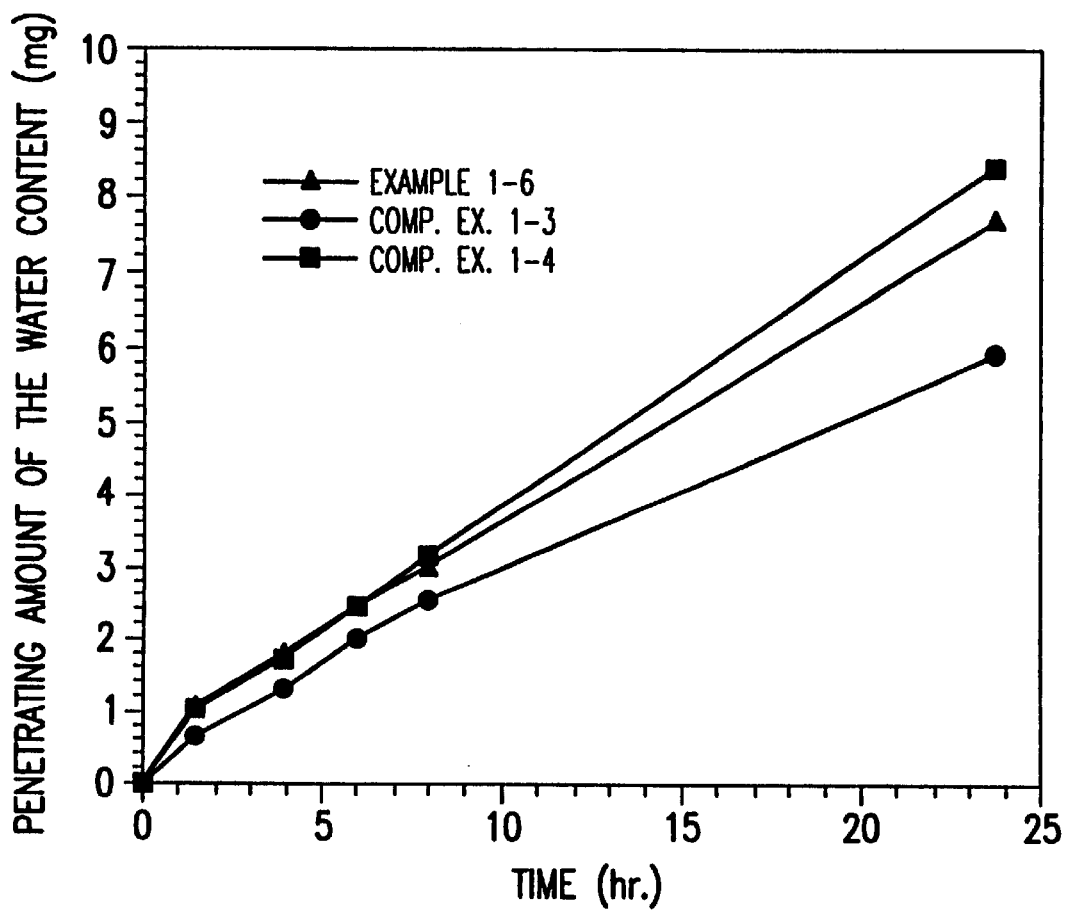
FIG. 7 is a chart comparing the penetrating amount of the water content in Example 1-6, Comparative example 1-3, and Comparative example 1-4.

The measurement of the penetrating amount of the water content has been performed by coating the lipstick which was prepared by the various formulation, on the filter paper, and by measuring the change of the amount of water content. The results are shown in FIG. 7.

In comparative example 1-3, the obtained lipstick had high blockage nature and had a little of the penetrating amount of the water content, since the lipstick was not comprised a lot of the water content. Thereupon, in case of comparing Example 1-6 with Comparative example 1-3, it was shown that the penetrating amount of the water content of Example 1-6 was less than that of Comparative example 1-3.

Accordingly, it is suggested that the hydrous composition of the present invention is rich in water-holding capacity, and furthermore, is stable as compared with the conventional products.

(2) Hydrous Composition Comprising a Hydrous Stabilizer

In the following, it will be explained the present invention in further detail from the examples. However, the present invention should not be limited to the following examples. Also, the compounding amount is expressed as parts by weight unless otherwise stated.

In first, the inventors were studied about the physical properties of the hydrous composition in accordance with the present invention. Namely, it was prepared the hydrous composition which comprising HP-β-CD, water, and a hydrous stabilizer or a humectant under the following formulation, and was studied the separation stability at high temperature of said composition.

[Separation stability]

o: It was not observed the separation of the water phase and the oil phase even after kept the composition in 8 hours at 90° C.

Δ: It was observed the separation of the water phase and the emulsion phase in a part of the composition after kept the composition in 1 hour at 80° C.

x: It was observed the separation of the water phase and the oil phase after kept the composition in 1 hour at 80° C.

TABLE 4

|  | Comp. ex. | | | | Example | |
| --- | --- | --- | --- | --- | --- | --- |
|  | 2-1 | 2-2 | 2-3 | 2-4 | 2-1 | 2-2 |
| Cholesteryl ester of macadamia nut oil fatty acid | 70 | 70 | 70 | 70 | 70 | 70 |
| Ion-exchanged water | 20 | 20 | 20 | 20 | 20 | 20 |
| HP-β-CD | 0 | 10 | 10 | 10 | 10 | 10 |
| Glycerin | 0 | 0 | 2 | 0 | 0 | 0 |
| 1,3-Butylene glycol | 0 | 0 | 0 | 2 | 0 | 0 |
| Alkylated polysiloxane polyethylene copolymer | 0 | 0 | 0 | 0 | 2 | 0 |
| Alkyl silicated Anhydrous silicate | 0 | 0 | 0 | 0 | 0 | 2 |
| Separation stability | X | Δ | Δ | Δ | ○ | ○ |

As is clear from the above-described results, in Comparative example 2-1, the separation in the water phase and the oil phase was observed in case of keeping the composition in 1 hour at 80?. Also, in Comparative example 2-2 to 2-4, the separation in a part of the water phase and the emulsion phase were observed in case of keeping the composition in 1 hour at 80° C. On the other hand, in Example 2-1 and 2-2, the separation in the water phase and the oil phase was not observed even in case of keeping the composition in 8 hours at 90° C. Accordingly, it is suggested that the hydrous composition of the present invention had high separation stability at high temperature.

Further, the inventors were performed the DSC measurement by using said Example 2-1, Example 2-2, and Comparative examples 2-1 to 2-3 under the following condition.

[DSC Measurement]

Measuring instrument measured by using Seiko Instruments Inc. DSC-100
Measuring condition

| Rate (Heating rate) | 5° C./min |
| --- | --- |
| Amount of the sample | 15.0 mg |
| Cell | Ag |
| Control cell | Al$_2$O$_3$ |
| measured at the open condition | |
| Temperature range | RT to 150° C. |

Figure 9A:
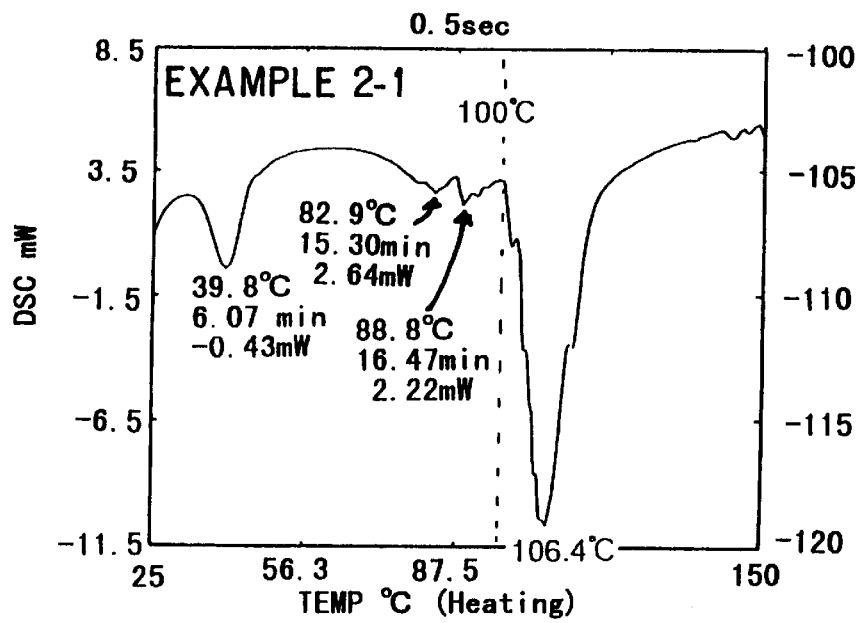
FIG. 9 are spectrum views of DSC measurement in Example 2-1 and 2-2.
Figure 9B:
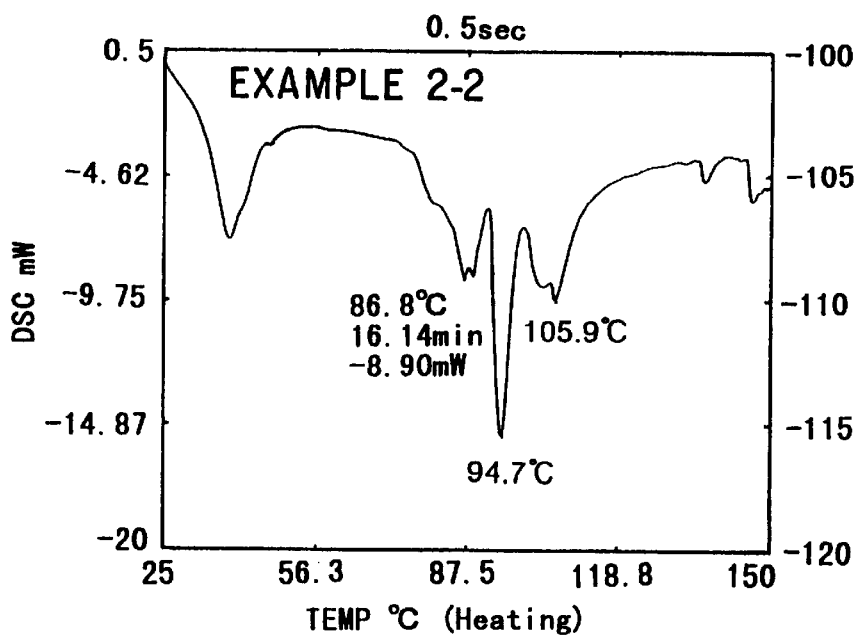

The results of DSC measurement are shown in FIG. 8 and FIG. 9.

As is clear from FIG. 8, in Comparative example 2-1, the maximum peak of DSC measurement was observed at 73.1° C. In Comparative example 2-2 which was added HP-β-CD, the maximum peak of DSC measurement was observed at 83.5° C. Both Comparative examples 2-1 and 2-2 were not observed the large peak after the maximum peak. Accordingly, it is thinkable that the water content was evaporated at 50 to 90° C. in Comparative examples 2-1 and 2-2.

In Comparative example 2-3 that was compounded glycerin which was the humectant used in general, the peak of DSC measurement was observed at in the vicinity of 80° C., and the gently curve was described even at the temperature over the peak. So, it can gathered that the water content was gradually evaporated. It is thinkable that this is due to the moisture ability of glycerin which was comprised in the composition. However, as for the water-holding at high temperature, the composition had a lack in stability.

On the other hand, in considering about Examples 2-1 and 2-2, each of the maximum peak of the DSC measurement were observed at more than 90° C. such as 106.4° C. and 94.7° C. respectively. Accordingly, it is suggested that the maximum peak of the temperature became more than 90° C. by adding the hydrous stabilizer of the present invention, and the composition which was improved the water-holding capacity at high temperature can be obtained.

Further, the inventors were studied about the water evaporation rate of said Examples 2-1 and 2-2.

Figure 10:
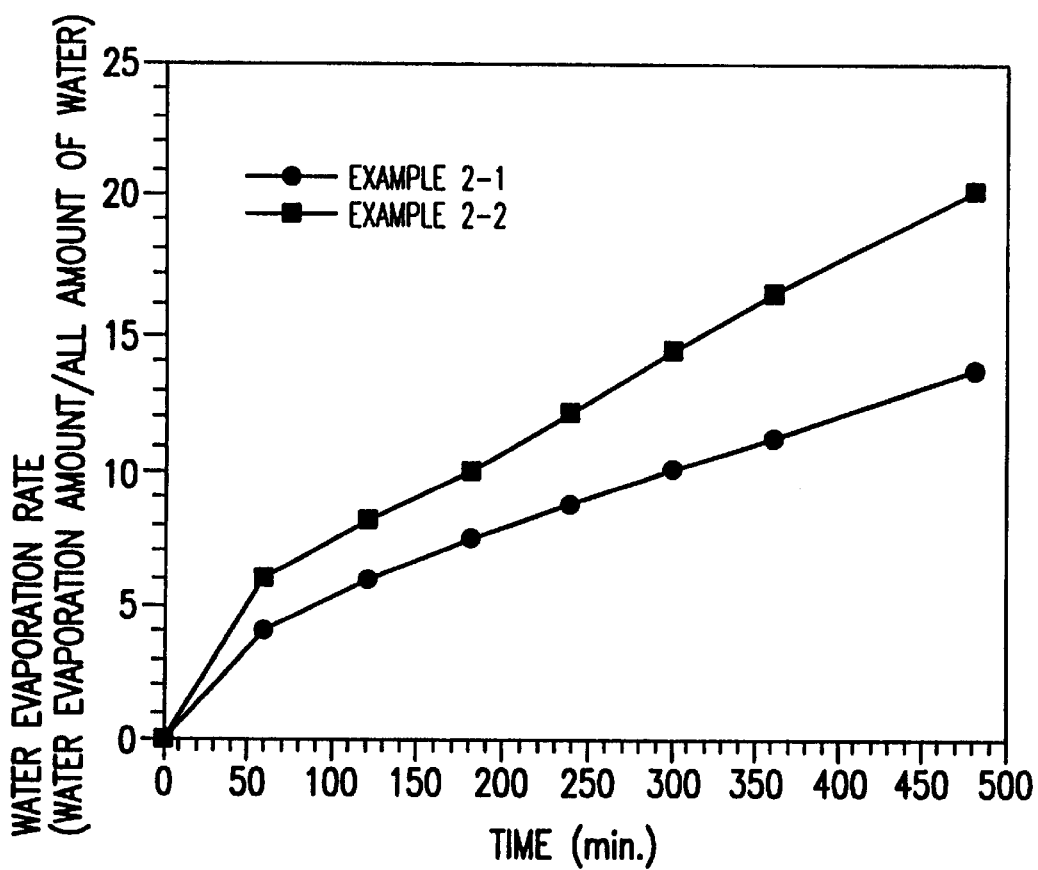
FIG. 10 is the results of the measurements of water evaporation rate which was performed by using Example 2-1 and Example 2-2.

The results are shown in FIG. 10.

As is clear from the drawing, in comparing with the results of Examples 2-1 and 2-2, the water evaporation rate of Example 2-1 was less than that of Example 2-2, the disparity was widened with passage of time. Namely, it was cleared that the side which was compounded alkylated polysiloxane polyethyleneglycol copolymer had low water evaporation rate in case of keeping in a long period of time and at high temperature.

Next, Example 2-3 and Comparative example 2-5 which removed HP-?-CD from the formulation of Example 2-3, were prepared as shown in the following formulation. And the compositions were taken on the preparation and were observed by microscope. And, DSC measurement was performed under the same condition as the above-described condition. In Example 2-3 and Comparative example 2-5, squalane was compounded for adjusting the viscosity.

Figure 11A:
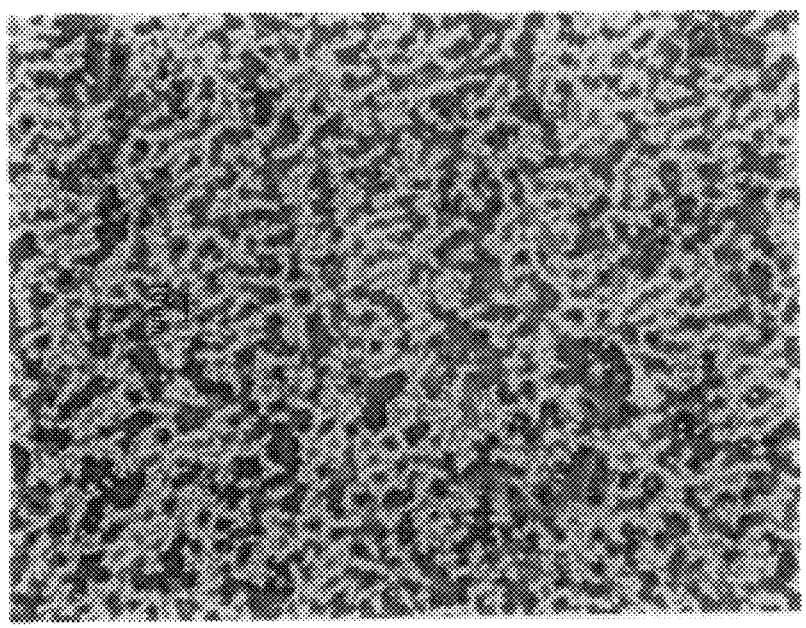
FIG. 11 are microphotographs which shows the hydration properties of Example 2-3 and Comparative example 2-5.
Figure 11B:
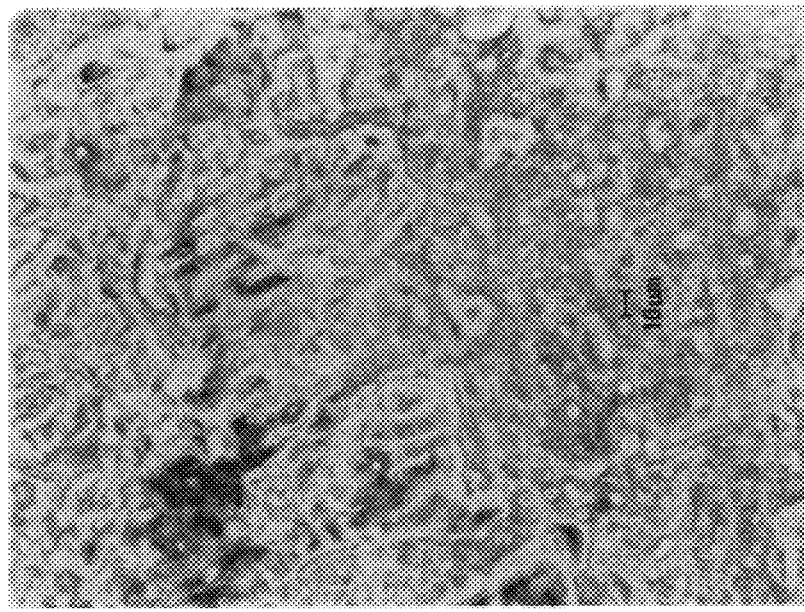
Figure 12A:
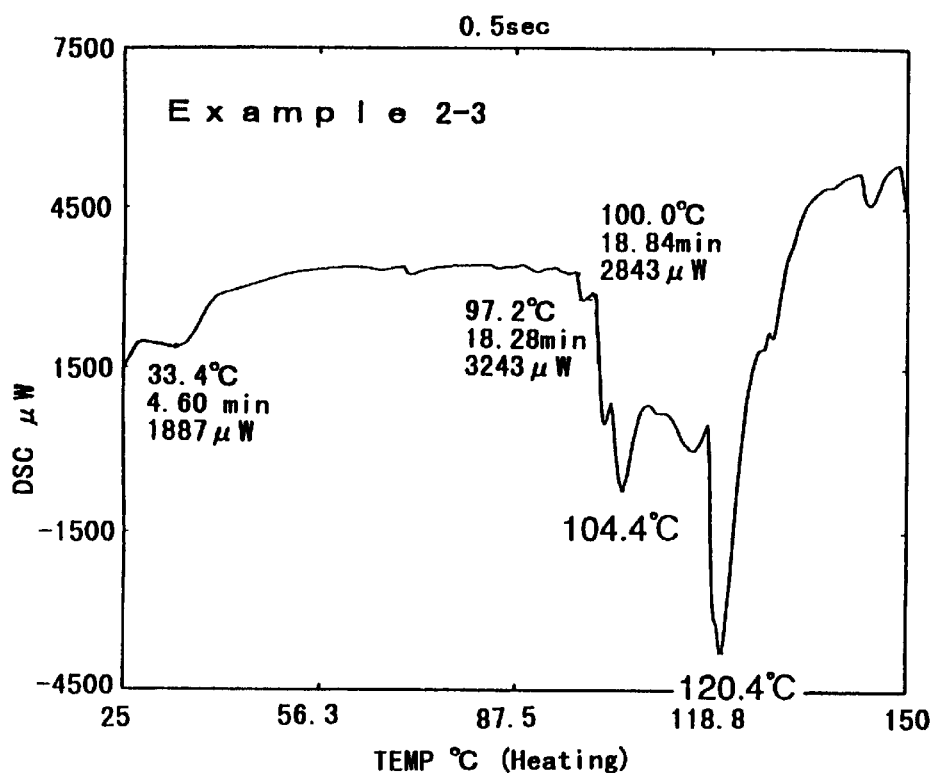
FIG. 12 are spectrum views of DSC measurement in Example 2-3 and Comparative example 2-5.
Figure 12B:
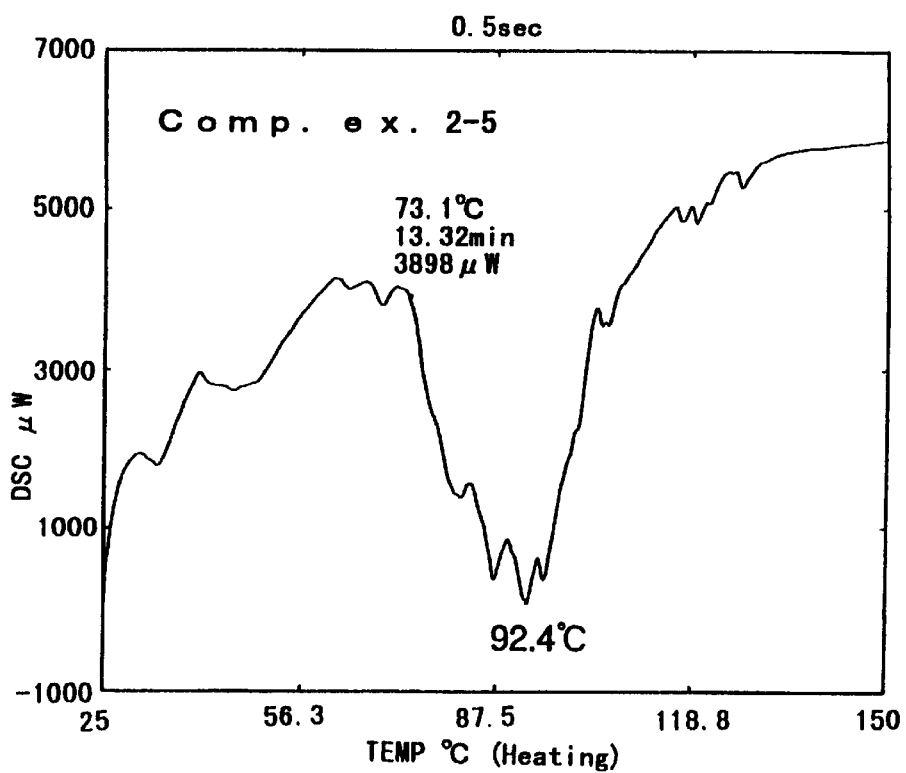

The microphotographs which were obtained by microscope observation are shown in FIG. 11. The results are shown in Table-4 together with its formulation. Also, the results of DSC measurement are shown in FIG. 12.

TABLE 5

|  | Example 2-3 | Comp. ex. 2-5 |
|---|---|---|
| Cholesteryl ester of macadamia nut oil fatty acid | 70 | 70 |
| Ion-exchanged water | 20 | 20 |
| HP-β-CD | 10 | 0 |
| Alkylated polysiloxane polyethylene copolymer | 2 | 2 |
| Squalane (adjusting viscosity) | 20 | 20 |
| Diameter of emulsion particle (μm) | 1 to 3 | not existed |
| Form of the composition | creamlike in uniformly | ununiformity (separation into two phases) |

As is clear from the above-described results and microphotographs, in Example 2-3 which was compounded HP-β-CD, the emulsion particle whose form was uniform creamlike and whose particle diameter was 1 to 3 μm, was existed. And it is thinkable that the emulsification was performed in stable. On the other hand, in Comparative example 2-5 which removed HP-β-CD from Example 2-3, the emulsion particle was not existed and the composition was separated into the oil phase and the water phase, therefore the emulsification cannot performed in stable.

Next, in case of comparing the results of DSC measurement in FIG. 12, it was understood that the striking disparity of water evaporation temperature was existed between Example 2-3 and Comparative example 2-5. Namely, in Comparative example 2-5 which removed HP-β-CD from Example 2-3, the peak of water evaporation temperature was observed at 70 to 100° C. On the other hand, in Example 2-3 which compounded HP-β-CD, the peak of water evaporation temperature was observed at a range between 100 to 130° C. From these results, it is suggested that the composition of the present invention had the high water-holding capacity even under the severe circumstance more than 90° C.

Further, the inventors were studied about the effects of the compounding of the HACD.

TABLE 6

|  | Comp. ex. | Example | | |
|---|---|---|---|---|
|  | 2-6 | 2-4 | 2-5 | 2-6 |
| Cholesteryl ester of macadamia nut oil fatty acid | 70 | 70 | 70 | 70 |
| Ion-exchanged water | 20 | 20 | 20 | 20 |
| HE-β-CD | — | 10 | — | — |
| HP-β-CD | — | — | 10 | — |
| HB-β-CD | — | — | — | 10 |
| Alkylated polysiloxane polyethylene copolymer | 2 | 2 | 2 | 2 |
| Diameter of emulsion particle (μm) | not existed | 1 to 3 | 1 to 3 | 1 to 3 |
| Form of the composition | separation | cream like | cream like | cream like |

As is clear from the above-described results, in Comparative example 2-6 which was not compounded the HACD, the emulsion particle cannot be formed and the composition was separated into the water phase and the oil phase. On the other hand, in Example 2-4 to 2-6 which compounded the HACD, the emulsion particle were formed the small sphere whose diameter were 1 to 3 μm, and the excellent composition which is creamlike can be obtained.

Further, the inventors were prepared the lipstick (Example 2-7) which compounded the composition of Example 2-1, and the lipstick (Comparative example 2-7) which directly compounded the same amount as Example 2-1 of HP-β-CD, water, cholesteryl ester of macadamia nut oil fatty acid, and alkylated polysiloxane polyethylene copolymer. And, the visual observation (aggregation of coloring agent), change of the water content of keratin, and the penetrating amount of the water content, were compared by using these lipsticks which were prepared as above for evaluating the hydration properties at the time of the products were formed. These various lipsticks were prepared by the following process. The composition of the various lipsticks are shown in Table-7 together with the results of visual observation.

(Process 1; Example 2-7)

The hydrous composition was prepared in advance (cf. Example 2-1). The hydrous composition was added to the lipstick bases which were dissolved at 80° C. After stirred it 10 minutes by disper stirring, the obtained composition was kept in 5 minutes at 90° C.

(Process 2; Comparative example 2-7) The lipstick bases were dissolved at 80° C. And after added and dissolved cholesteryl ester of macadamia nut oil fatty acid and alkylated polysiloxane polyethylene copolymer to it, adding the solution of HP-β-CD which was dissolved into water, to the oil phase, stirring it 10 minutes by disper stirring. And, the obtained composition was kept in 5 minutes at 90° C.

TABLE 7

|  | Comp. ex. 2-7 | Example 2-7 |
|---|---|---|
| A. Lipstick bases | | |
| Carnauba wax | 0.5 | 0.5 |
| Candelilla wax | 5.0 | 5.0 |
| Ceresin | 10.0 | 10.0 |
| Squalane | 11.0 | 11.0 |
| Liquid paraffin | 30.0 | 30.0 |
| Glyceryl isostearate | 14.8 | 14.8 |
| Glyceryl diisostearate | 8.3 | 8.3 |
| B. Hydrous composition | | |
| Hydrous composition Of Example 2-1 | — | 20.4 |
| HP-β-CD | 2.0 | — |
| Cholesteryl ester of macadamia nut oil fatty acid | 14.0 | — |
| Alkylated polysiloxane polyethylene copolymer | 0.4 | — |
| Ion-exchanged water | 4.0 | — |
| Visual Observation | ununiformity by separated into the oil phase and the emulsion phase | the emulsion particle was uniformly dispersed |

As is clear from the above-described results, as shown in Comparative example 2-7, in the case where the various ingredients of the hydrous composition were separately compounded, the obtained composition became ununiform by the separation into the oil phase and the emulsion phase, and had lack in the separation stability. In the case where the various ingredients were added separately to the composition, water was adsorbed to alkylated polysiloxane polyethylene copolymer used in the present invention as the hydrous stabilizer. And, silicone is inferior in compatibility with respect to the hydrocarbon type oily component. So, it is thinkable that the composition was separated into the emulsion phase of silicone active agent and the oil phase of hydrocarbon.

On the other hand, in Example 2-7 which comprising the hydrous composition of the present invention, the hydrous composition was uniformly dispersed. It is thought that the emulsion particle is considerably fine and has high dispersibility as shown in Example 2-3.

Accordingly, the hydrous composition of the present invention has high separation stability and can be favorably kept the water phase into the oil phase.

(3) Hydrous Composition Comprising a Clay Mineral

In first, the inventors paid attention to a clay mineral as the materials which improved the separation stability. And, they prepared the hydrous composition by the formulation of the following Table-8, and studied about the physical properties of the hydrous composition of the present invention. And, it has been studied by using HP-β-CD as the HACD, cholesteryl ester of macadamia nut oil fatty acid as the cholesterol ester, and synthetic sodium magnesium as the clay mineral. The following composition is shown as parts by weight.

[Separation Stability at High Temperature]

○: It was not observed the separation of the water phase and the oil phase even after kept the composition 8 hours at 90° C.

Δ: It was observed the separation of the water phase and the emulsion phase in a part of the composition after kept the composition in 1 hour at 80° C.

x: It was observed the separation of the water phase and the oil phase or the emulsion phase after passed 1 hour at 80° C.

TABLE 8

|  | Comp. ex. 3-1 | Comp. ex. 3-2 | Example 3-1 |
|---|---|---|---|
| Cholesteryl ester of macadamia nut oil fatty acid | 60 | 60 | 60 |
| Ion-exchanged water | 40 | 40 | 40 |
| HP-β-CD | 0 | 10 | 10 |
| Synthetic sodium magnesium silicate | 0 | 0 | 5 |
| Diameter of emulsion particle ($\mu$m) | 1–10 | 1–5 | — |
| Form of the composition | crumbly | had a visco-elasticity | had a visco-elasticity |
| Separation stability | x | Δ | ○ |

As is clear from the above-described results, Comparative example 3-1 which was obtained by mixing the cholesterol ester and water, became crumbly itself, and had a large emulsion particle, and it was observed the separation into the water phase and the oil phase at high temperature. And also, Comparative example 3-2 which compounded HP-β-CD to Comparative example 3-1, had small diameter of emulsion particle and had a viscoelasticity. However, in case of keeping the composition at high temperature, it was observed the separation of the water phase and the emulsion phase in a part of the composition. On the other hand, in Example 3-1, the emulsion particle of sphere shape cannot observed. However the excellent hydrous composition which had a viscoelasticity and had a high separation stability even at high temperature can be obtained.

Figure 13A:
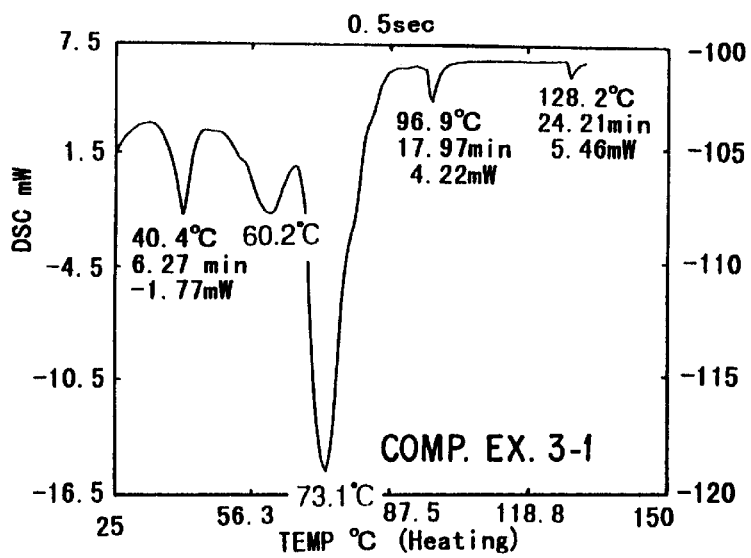
FIG. 13 are spectrum views of DSC measurement in Example 3-1, Comparative example 3-1 and 3-2.
Figure 13B:
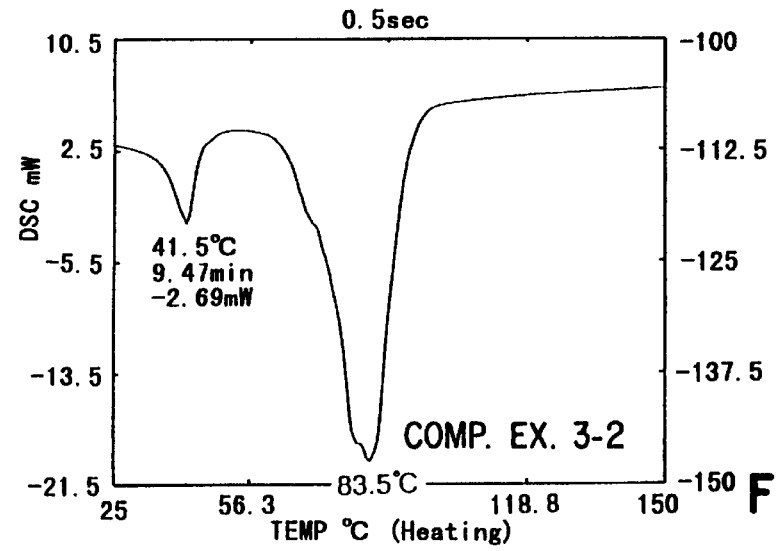
Figure 13C:
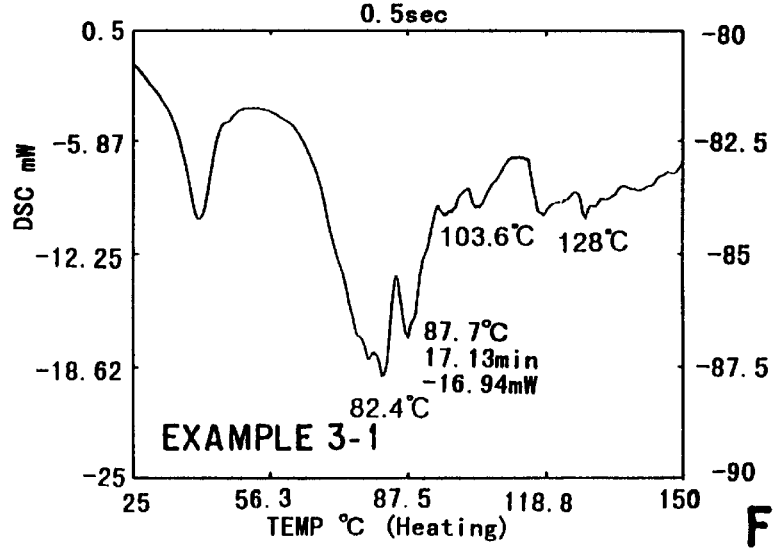

Further, the inventors were performed the DSC measurement about the Example 3-1, Comparative example 3-1, and 3-2 by the following condition. The results are shown in FIG. 13.

[DSC Measurement]

| Measuring instrument | Seiko Instruments Inc DSC-100 |
|---|---|
| Measuring condition | |
| Rate (Heating rate) | 5° C./min |
| Amount of the sample | 15.0 mg |
| Cell | Ag |
| Control cell measured at the open condition | $Al_2O_3$ |
| Temperature range | RT to 150° C. |

As is clear from the drawings, in Comparative example 3-1, the maximum peak was 73.1 ° C. and was lower than that of Comparative example 3-2 and Example 3-1.

The maximum peak of Comparative example 3-2 and Example 3-1 were 83.5° C. and 82.4° C. respectively, and were almost equivalent. However, in Example 3-1, the peak were observed at 103.6° C. and 128° C., and the evaporation of the water content can be observed even more than 100° C. It was thought as the peak of water which is held in stable, since synthetic sodium magnesium silicate take water into the middle of the phases.

Accordingly, from the physical properties of the composition and the results of DSC measurement, it is suggested that the composition in accordance with the present invention is the composition which has high separation stability and is also excellent in water-holding.

Next, the inventors were studied about the effects of the compounding of the hydroxyalkylated cyclodextrin.

TABLE 9

|  | Comp. ex. | Example | | |
|---|---|---|---|---|
|  | 3-3 | 3-2 | 3-3 | 3-4 |
| Cholesteryl ester of macadamia nut oil fatty acid | 68 | 68 | 68 | 68 |
| Ion-exchanged water | 20 | 20 | 20 | 20 |
| HP-β-CD | — | 10 | — | — |
| HE-β-CD | — | — | 10 | — |
| HB-β-CD | — | — | — | 10 |
| Synthetic sodium magnesium silicate | 5 | 5 | 5 | 5 |
| Diameter of emulsion particle ($\mu$m) | — | — | — | — |
| Form of the hydrous composition | separation | had a visco-elasticity | had a visco-elasticity | had a visco-elasticity |
| Separation stability | — | — | — | — |

As is clear from the above-described results, in Comparative example 3-3 which was not compounded the HACD at all, the separation of the water phase and the oil phase at high temperature was observed. On the other hand, in Examples 3-2 to 3-4 which were compounded HP-β-CD, HE-β-CD, and HB-β-CD respectively, each of the composition had a viscoelasticity, and became excellent in the separation stability at high temperature.

Accordingly, it is suggested that the composition which is favorably improved the separation stability can be obtained, by compounding the hydroxyalkylated cyclodextrin.

Next, the inventors were studied about the relationships between the compounding amount of the clay mineral and separation stability of the hydrous composition at high temperature.

TABLE 10

|  | Example | | | | | |
|---|---|---|---|---|---|---|
|  | 3-5 | 3-6 | 3-7 | 3-8 | 3-9 | 3-10 |
| Cholesteryl ester of macadamia nut oil fatty acid | 68 | 68 | 68 | 68 | 68 | 68 |
| Squalane | 20 | 20 | 20 | 20 | 20 | 20 |
| Synthetic sodium magnesium silicate | 0 | 1 | 3 | 5 | 10 | 20 |
| HP-β-CD | 10 | 10 | 10 | 10 | 10 | 10 |
| Glycerin | 2 | 2 | 2 | 2 | 2 | 2 |
| Water | 20 | 20 | 20 | 20 | 20 | 20 |
| Separation stability | X | Δ | Δ | ○ | ○ | ○ |

As is clear from the above-described results, in the condition which was not compounded synthetic sodium magnesium silicate, the separation stability at high temperature is bad, and the separation of the water phase and the oil phase or the emulsion phase was confirmed. Also, in the case where 1 to 3 parts by weight of synthetic sodium magnesium silicate were compounded, though the stability were improved, the improvement was not sufficient. On the other hand, in the case where 5 to 20 parts by weight of synthetic sodium magnesium silicate were compounded, separation stability at high temperature were improved.

Next, the inventors were prepared the hydrous composition under the following formulation by using other clay minerals, and were studied about the emulsion stability.

TABLE 11

|  | Example | | | | |
|---|---|---|---|---|---|
|  | 3-11 | 3-12 | 3-13 | 3-14 | 3-15 |
| Cholesteryl ester of macadamia nut oil fatty acid | 68 | 68 | 68 | 68 | 68 |
| Squalane | 20 | 20 | 20 | 20 | 20 |
| Lithium teniorite | 5 | — | — | — | — |
| Sodium tetra silicate mica | — | 5 | — | — | — |
| Lithium hectorite | — | — | 5 | — | — |
| Mica | — | — | — | 5 | — |
| Dimethyl stearyl ammonium hectorite | — | — | — | — | 5 |
| HP-β-CD | 10 | 10 | 10 | 10 | 10 |
| Glycerin | 2 | 2 | 2 | 2 | 2 |
| Water | 20 | 20 | 20 | 20 | 20 |
| Separation stability | ○ | ○ | ○ | Δ | ○ |

From the above-described results, in case of using lithium tennessee, sodium tetra silicate mica, lithium hectorite which were the swelling type clay mineral as like synthetic sodium magnesium silicate, the separation stability were improved, as like the case used synthetic sodium magnesium silicate. And, in case of compounding dimethylstearyl ammonium hectorite which was the organophilic smectite, the improvement of separation stability can be observed.

On the other hand, in case of compounding mica which was the non-swelling type clay mineral, separation stability was improved in a part, but the sufficient stability cannot be obtained.

Next, the inventors were studied about the compounding of hydrophobic silica for improving the separation stability by compounding a little amount of the clay mineral and for obtaining a further fine emulsion particle, since the clay minerals were caused the surface roughness and were worsened the feeling of use in some time. The diameter of emulsion particle was observed by using light microscope. The evaluation was studied about separation stability at high temperature and water- holding capacity.

[Water-Holding Capacity]
  ○: Water evaporation rate after passed 8 hours at 90° C. was less than 20%
  x: Water evaporation rate after passed 8 hours at 90° C. was 20% or more

TABLE 12

|  | Example | | | | | | |
|---|---|---|---|---|---|---|---|
|  | 3-16 | 3-17 | 3-18 | 3-19 | 3-20 | 3-21 | 3-22 |
| Cholesteryl ester of macadamia nut oil fatty acid | 68 | 68 | 68 | 68 | 68 | 68 | 68 |
| Squalane | 20 | 20 | 20 | 20 | 20 | 20 | 20 |
| Hydrophobic silica | 2 | 2 | 2 | 2 | 2 | 2 | 2 |

TABLE 12-continued

|  | Example | | | | | | |
|---|---|---|---|---|---|---|---|
|  | 3-16 | 3-17 | 3-18 | 3-19 | 3-20 | 3-21 | 3-22 |
| Synthetic sodium magnesium silicate | 3 | — | — | — | — | — | — |
| Lithium teniorite | — | 3 | — | — | — | — | — |
| Sodium tetra silicate mica | — | — | 3 | — | — | — | — |
| Lithium hectorite | — | — | — | 3 | — | — | — |
| Mica | — | — | — | — | 3 | — | — |
| Dimethyl stearyl ammonium hectorite | — | — | — | — | — | 3 | — |
| Aluminium magnesium silicate processed with distearyl-dimethyl ammonium chloride | — | — | — | — | — | — | 3 |
| HP-β-CD | 10 | 10 | 10 | 10 | 10 | 10 | 10 |
| Glycerin | 2 | 2 | 2 | 2 | 2 | 2 | 2 |
| Water | 20 | 20 | 20 | 20 | 20 | 20 | 20 |
| Diameter of emulsion particle (?m) | 1 to 8 | 1 to 8 | 1 to 8 | 1 to 8 | 3 to 20 | 1 to 3 | 1 to 3 |
| Separation stability | ○ | ○ | ○ | ○ | ○ | ○ | ○ |
| Water-holding capacity | ○ | ○ | ○ | ○ | ○ | ○ | ○ |

As is clear from the above-described results, in the case where hydrophobic silica and the clay mineral were compounded with combining, the improvement of separation stability at 90° C. can be observed in all clay minerals. And, in the case where 3 parts by weight of synthetic sodium magnesium silicate was compounded in separately, the separation stability at high temperature was not sufficient (in Table-7, Example 3-4). However, in the case where hydrophobic silica was compounded, the sufficient separation stability can be obtained. Also, since the compounding amount of the clay mineral was small, it was not caused the problems in the feeling of use such as surface roughness.

Further, when the inventors measured the diameter of emulsion particle of each composition by using light microscope, the fine emulsion particle whose diameter were 1 to 8 μm were observed in the swelling type clay mineral and the organophilic smectite. On the other hand, in mica which is the non-swelling type clay mineral, the considerable large emulsion particle whose diameter was 3–20 μm was formed.

Accordingly, in the case where hydrophobic silica was compounded, the separation stability at high temperature was improved and the excellent hydrous composition which had fine emulsion particle was also formed, by compounding just a small amount of clay mineral.

Next, by using HE-β-CD, HP-β-CD and HB-β-CD, the study were performed about the properties of the composition which were compounded with hydrophobic silica. In this place, synthetic sodium magnesium silicate was used as the clay mineral.

TABLE 13

|  | Ex. 3-23 | Ex. 3-24 | Ex. 3-25 |
|---|---|---|---|
| Cholesteryl ester of macadamia nut oil fatty acid | 68 | 68 | 68 |
| Squalane | 20 | 20 | 20 |
| Hydrophobic silica | 2 | 2 | 2 |
| Synthetic sodium magnesium silicate | 5 | 5 | 5 |
| HE-β-CD | 10 | — | — |
| HP-β-CD | — | 10 | — |

TABLE 13-continued

|  | Ex. 3-23 | Ex. 3-24 | Ex. 3-25 |
|---|---|---|---|
| HB-β-CD | — | — | 10 |
| Glycerin | 2 | 2 | 2 |
| Water | 20 | 20 | 20 |
| Diameter of emulsion particle (μm) | 2 to 8 | 2 to 8 | 2 to 8 |
| Separation stability | ○ | ○ | ○ |
| Form of the composition | had a viscoelasticity | had a viscoelasticity | had a viscoelasticity |

As is clear from the above-described results, in the case where hydrophobic silica was combined with any one of said HACD, the emulsion particle which had a viscoelasticity and fine particle diameter can be formed. In particular, it was more preferable to compound with HE-β-CD or HP-β-CD, since the fine emulsion particle was formed.

Next, the inventors were studied about the compounding amount of hydrophobic silica. In this place, synthetic sodium magnesium silicate was used as the clay mineral.

TABLE 14

| | Example | | | | | | |
|---|---|---|---|---|---|---|---|
| | 3-26 | 3-27 | 3-28 | 3-29 | 3-30 | 3-31 | 3-32 |
| Cholesteryl ester of macadamia nut oil fatty acid | 68 | 68 | 68 | 68 | 68 | 68 | 68 |
| Squalane | 20 | 20 | 20 | 20 | 20 | 20 | 20 |
| Hydrophobic silica | 0 | 0.01 | 1 | 5 | 10 | 20 | 25 |
| Synthetic sodium magnesium silicate | 3 | 3 | 3 | 3 | 3 | 3 | 3 |
| HP-β-CD | 10 | 10 | 10 | 10 | 10 | 10 | 10 |
| Glycerin | 2 | 2 | 2 | 2 | 2 | 2 | 2 |
| Water | 20 | 20 | 20 | 20 | 20 | 20 | 20 |
| Compounding amount of hydrophobic silica (% by weight) | 0 | 0.016 | 0.8 | 3.9 | 7.5 | 14.0 | 19.6 |
| Diameter of emulsion particle (μm) | — | 3 to 30 | 2 to 15 | 1 to 2 | to 1 | to 1 | to 1 |
| Separation stability | — | — | — | — | — | — | — |

As is clear from the above-described results, in the case where hydrophobic silica was not compounded at all, the separation stability was not improved, and the emulsion particle cannot observed. On the other hand, in the case where more than 20% by weight of hydrophobic silica were compounded, the improvement of the separation stability can be observed. However, the compounding amount of silica became large in relative, it sometimes worsened the feeling of use of the composition.

Accordingly, it is preferable to compound hydrophobic silica within a range of 0.01 to 20% by weight.

Next, the study was performed about the ratio of the compounding amount of hydrophobic silica and the clay mineral in the case where hydrophobic silica and the clay mineral were used by combining together.

In this place, synthetic sodium magnesium silicate was used as the clay mineral.

TABLE 15

| | Example | | | | | | |
|---|---|---|---|---|---|---|---|
| | 3-33 | 3-34 | 3-35 | 3-36 | 3-37 | 3-38 | 3-39 |
| Cholesteryl ester of macadamia nut oil fatty acid | 68 | 68 | 68 | 68 | 68 | 68 | 68 |
| Squalane | 20 | 20 | 20 | 20 | 20 | 20 | 20 |
| Hydrophobic silica | 2 | 2 | 2 | 2 | 2 | 2 | 2 |
| Synthetic sodium magnesium silicate | 0 | 1 | 3 | 5 | 7 | 10 | 20 |
| HP-β-CD | 10 | 10 | 10 | 10 | 10 | 10 | 10 |
| Glycerin | 2 | 2 | 2 | 2 | 2 | 2 | 2 |
| Water | 20 | 20 | 20 | 20 | 20 | 20 | 20 |
| Diameter of emulsion particle (μm) | 3 to 20 | 2 to 15 | 2 to 8 | 2 to 8 | 1 to 5 | — | — |
| Separation stability | ○ | ○ | ○ | ○ | ○ | ○ | ○ |

Figure 14A:
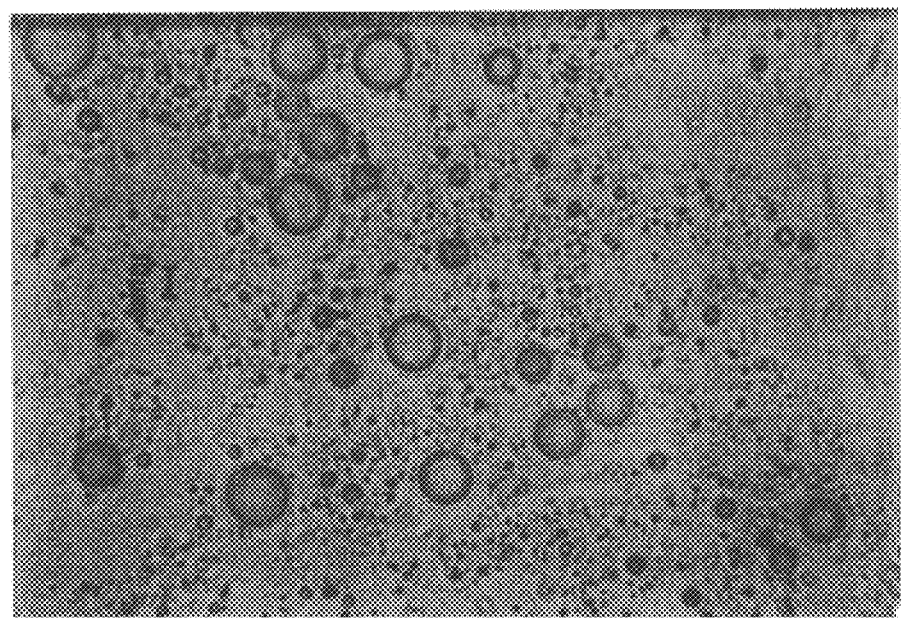
FIG. 14 are microphotographs which shows the hydrous composition of Example 3-33 to 3-37 and Example 3-39.
Figure 14B:
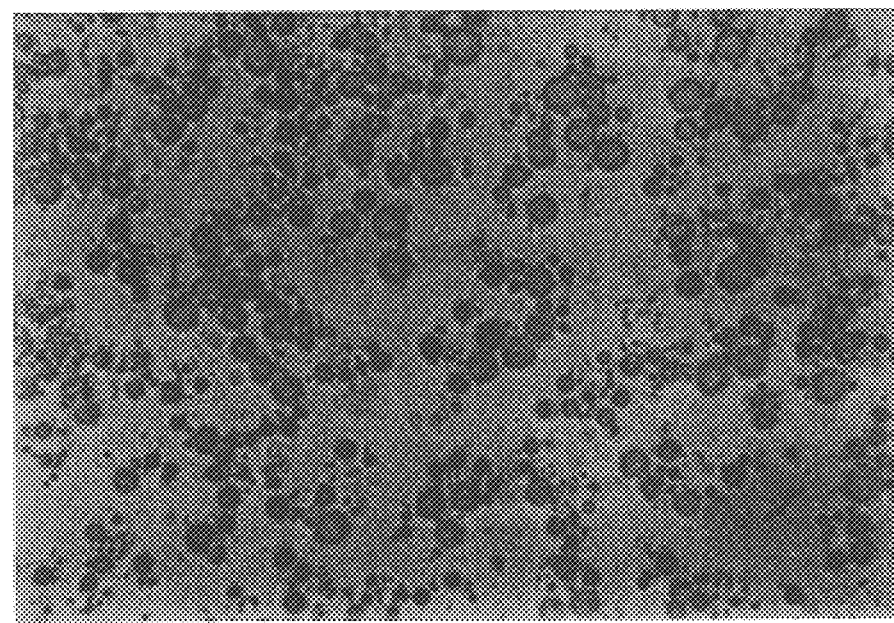
Figure 14C:
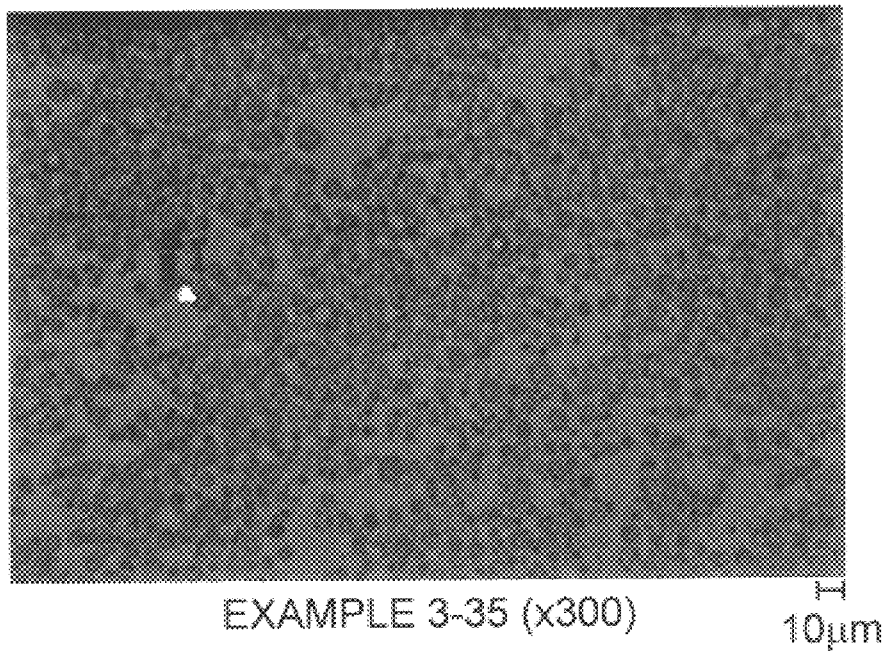
Figure 14D:
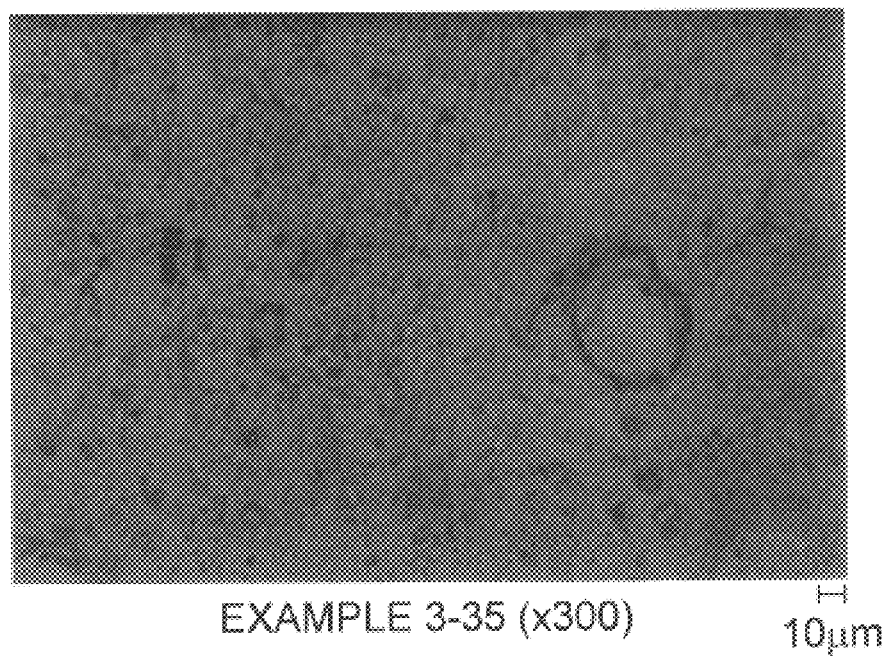
Figure 14E:
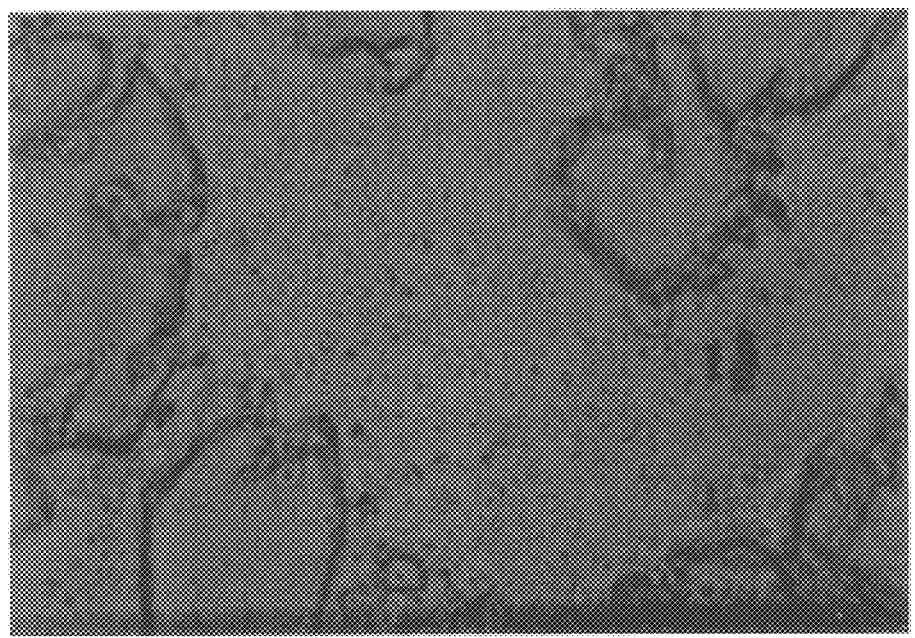
Figure 14F:
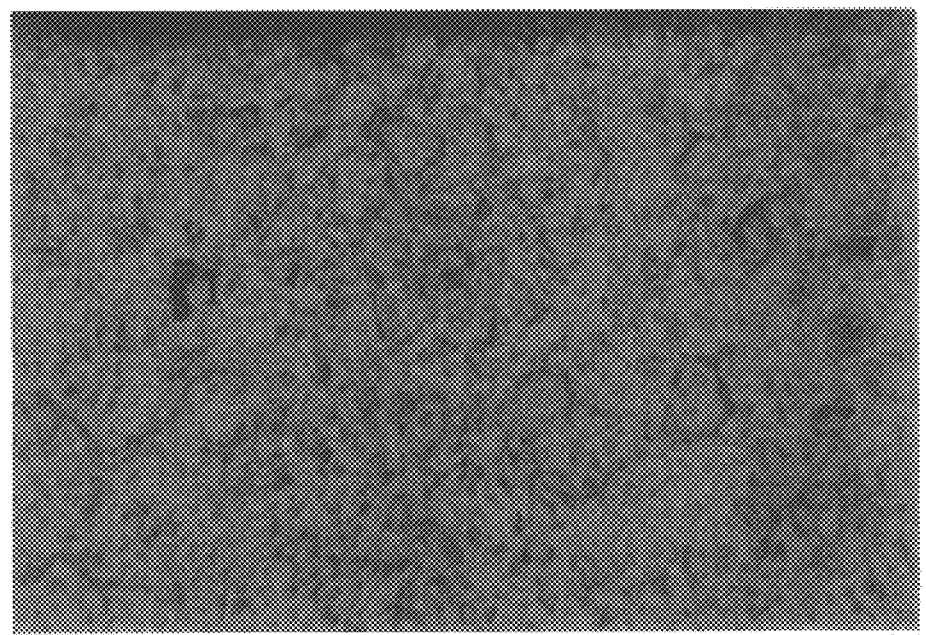

As is clear from the above-described results, in the case where hydrophobic silica was compounded, the excellent separation stability can be obtained in all the hydrous composition. Also, in measuring the diameter of emulsion particle, in the case where synthetic sodium magnesium silicate was not compounded, it was formed the emulsion particle whose diameter was 3 to 20 μm, and the fine emulsion particle was not formed (Example 3-33 and FIG. 14A). Also, in the case where more than 10 parts by weight of synthetic sodium magnesium silicate was compounded, though the separation of the water phase and the emulsion phase was not observed, the emulsion particle cannot be observed (Example 3-39 and FIG. 14F). On the other hand, in the case where 1 to 7 parts by weight of synthetic sodium magnesium silicate were compounded, it can formed the fine emulsion particle whose diameter was 1 to 15 μm (Example 3-34 to 3-37, FIGS. 14B to E).

Figure 15:
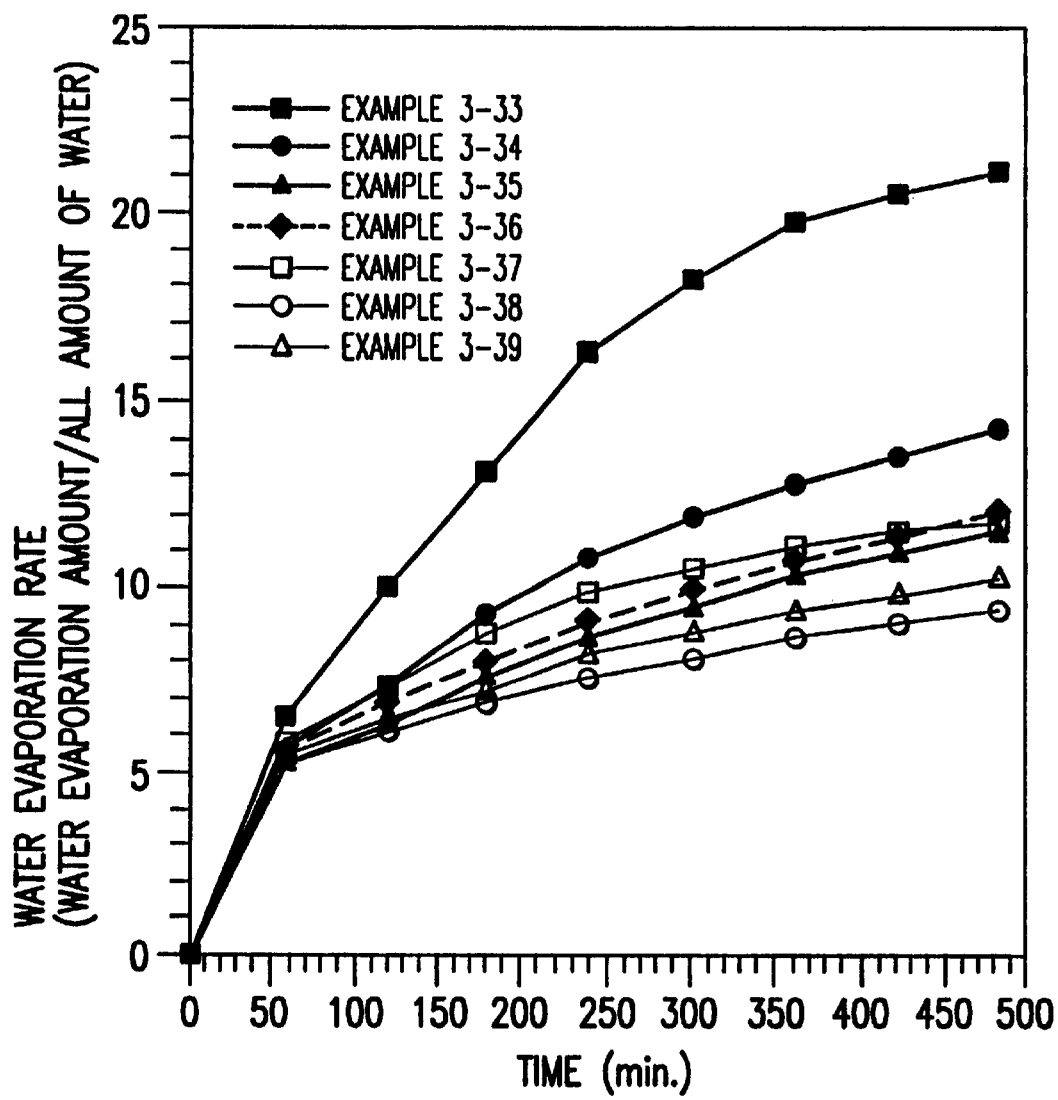
FIG. 15 shows the results of the measurements of water evaporation rate which was performed by using the hydrous compositions of Example 3-33 to 3-39.

Also, FIG. 15 is the results of the study of the water evaporation rate by using the above-described Example 3-33 to 3-39. As is clear from FIG. 15, the water evaporation rate was inhibited by compounding synthetic sodium magnesium silicate. Accordingly, it is suggested that the water-holding capacity was improved by the addition of clay mineral.

Accordingly, in the case where hydrophobic silica and the clay mineral were compounded by combining together, the ratio of the compounding amount of hydrophobic silica to the clay mineral was preferably 2:1 to 1:4.

Further, it will be shown the more concrete compounding examples of the present invention.

(1) Compounding Examples Used a Hydrous Composition Comprising a Cholesterol Ester Clathrate Each of the compounding examples had a large conductance ratio of the water content of keratin, and were excellent in water-holding capacity and keeping stability, and had no apprehension about the irritation for skin.

| Compounding example 1-1 | Skin lotion |
|---|---|
| A. Water phase part | |
| Glycerin | 10.0% by weight |
| Propylene glycol | 5.0 |
| Ethanol | 5.0 |
| Parahydroxybenzoic acid ester | 0.2 |
| Purified water | balance |

-continued

| Compounding example 1-1 | Skin lotion |
|---|---|
| B. Hydrous composition | |
| HP-β-CD | 0.4 |
| Cholesterol ester (Olive oil fatty acid) | 0.1 |
| Purified water | 0.5 |
| C. Oil phase part | |
| Cetyl isooctanoate | 4.0 |
| 2-Ethylhexyl 4-methoxycinnamate | 0.1 |

(Process)

Adding the solution of HP-β-CD which was dissolved into 0.1% by weight of purified water to the cholesterol ester of 60° C., and stirring it 10 minutes by a disper. And then, adding the rest of purified water (0.4% by weight) to it and stirring it 10 minutes by a homomixer, and the hydrous composition was prepared. After adding this hydrous composition to the water phase part, adding the oil phase part to it and stirring it 10 minutes by a homomixer, and the skin lotion was obtained.

| Compounding example 1-2 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous composition | |
| HP-β-CD | 1.0 |
| Cholesterol ester (Isostearic acid) | 3.5 |
| Glycerin | 0.5 |
| Glycerin | |
| Purified water | 2.0 |
| C. Other bases | |
| Coloring agent | q.s. |
| perfume | q.s. |
| Antiseptic | q.s. |

(Process)

Adding the solution of HP-β-CD which was dissolved into 0.5 parts by weight of purified water to the cholesterol ester of 60° C., and stirring it 10 minutes by a disper. And then, adding the rest of purified water (1.5 parts by weight) and glycerin to it and stirring it 10 minutes by a homomixer, and the hydrous composition was prepared. The lipstick bases were dissolved at 80° C., and the hydrous composition was added to this. After stirring it 10 minutes by a disper, adding coloring agent, perfume, and antiseptic to it, dispersing and stirring it, then the lipstick was formed.

| Compounding example 1-3 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous composition | |
| HP-β-CD | 1.0 |
| Cholesterol ester (Oleic acid) | 3.5 |
| Glycerin | 0.5 |
| Purified water | 2.0 |

-continued

| Compounding example 1-3 | Lipstick |
|---|---|
| C. Other bases | |
| Coloring agent | q.s. |
| Perfume | q.s. |
| Antiseptic | q.s. |

(Process)

The lipstick was obtained by the same process with Compounding example 1-2.

| Compounding example 1-4 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous composition | |
| HP-β-CD | 1.0 |
| Cholesterol ester (Isostearic acid) | 4.0 |
| Glycerin | 0.5 |
| Purified water | 1.5 |
| C. Other bases | |
| Coloring agent | q.s. |
| Perfume | q.s. |
| Antiseptic | q.s. |

(Process)

The lipstick was obtained by the same process with Compounding example 1-2.

| Compounding example 1-5 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous composition | |
| HE-β-CD | 1.0 |
| Cholesterol ester (Oleic acid) | 4.0 |
| Glycerin | 0.5 |
| Purified water | 1.5 |
| C. Other bases | |
| Coloring agent | q.s. |
| Perfume | q.s. |
| Antiseptic | q.s. |

(Process) The lipstick was obtained by the same process with Compounding example 1-2.

| Compounding example 1-6 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |

| Compounding example 1-6 | Lipstick |
|---|---|
| B. Hydrous composition | |
| HP-β-CD | 1.0 |
| Cholesteryl ester of macadamia nut oil fatty acid | 3.5 |
| Glycerin | 0.2 |
| Purified water | 2.0 |
| C. Other bases | |
| Coloring agent | q.s. |
| Perfume | q.s. |
| Antiseptic | q.s. |

(Process)

The lipstick was obtained by the same process with Compounding example 1-2.

(2) Hydrous composition comprising a hydrous stabilizer

Each of the compounding examples had a large conductance ratio of the water content of keratin, and were excellent in water-holding capacity and keeping stability, and had no apprehension about the irritation for skin.

| Compounding example 2-1 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous composition | |
| HP-β-CD | 1.0 |
| Cholesterol ester (Isostearic acid) | 3.5 |
| Alkylated polysiloxane polyethylene copolymer | 0.2 |
| Glycerin | 0.5 |
| Purified water | 1.0 |
| C. Other bases | |
| Coloring agent | q.s. |
| Perfume | q.s. |
| Antiseptic | q.s. |

(Process)

Dispersing alkylated polysiloxane polyethylene copolymer as the hydrous stabilizer into the cholesterol ester of 60° C., and adding the solution of HP-β-CD which was dissolved into 0.5 parts by weight of purified water to it, and stirring it 10 minutes by a disper. And then, adding the rest of purified water (1.5 parts by weight) and glycerin to it and stirring it 10 minutes by a homomixer, and the hydrous composition was prepared. The hydrous composition was added to the lipstick bases which were dissolved at 80° C. After stirring it 10 minutes by a disper, adding coloring agent, perfume, and antiseptic to it and dispersing and stirring it. And then, forming it and the lipstick was obtained.

| Compounding example 2-2 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |

| Compounding example 2-2 | Lipstick |
|---|---|
| B. Hydrous composition | |
| HP-β-CD | 1.0 |
| Cholesterol ester (Oleic acid) | 3.5 |
| Alkyl silicated anhydrous silicate | 0.2 |
| Glycerin | 0.5 |
| Purified water | 1.0 |
| C. Other bases | |
| Coloring agent | q.s. |
| Perfume | q.s. |
| Antiseptic | q.s. |

(Process)

The lipstick was obtained by the same process with Compounding example 2-1.

| Compounding example 2-3 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous composition | |
| HP-β-CD | 1.0 |
| Cholesterol ester (Stearic acid) | 3.5 |
| Glyceryl-modified silicone resin coated powder | 0.2 |
| Glycerin | 0.5 |
| Purified water | 2.0 |
| C. Other bases | |
| Coloring agent | q.s. |
| Perfume | q.s. |
| Antiseptic | q.s. |

(Process)

The lipstick was obtained by the same process with Compounding example 2-1.

| Compounding example 2-4 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous composition | |
| HP-β-CD | 1.0 |
| Cholesterol ester (Oleic acid) | 3.5 |
| Dextrin fatty acid ester | 0.2 |
| Glycerin | 0.5 |
| Purified water | 1.5 |
| Coloring agent | q.s. |
| Perfume | q.s. |
| Antiseptic | q.s. |

(Process)

The lipstick was obtained by the same process with Compounding example 2-1.

| Compounding example 2-5 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous composition | |
| HE-β-CD | 1.0 |
| Cholesterol ester (Oleic acid) | 3.5 |
| Alkylated polysiloxane polyethylene copolymer | 0.2 |
| Glycerin | 0.5 |
| Purified water | 1.5 |
| C. Other bases | |
| Coloring agent | q.s. |
| Perfume | q.s. |
| Antiseptic | q.s. |

(Process)

The lipstick was obtained by the same process with Compounding example 2-1.

| Compounding example 2-6 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous composition | |
| HB-β-CD | 1.0 |
| Cholesteryl ester of macadamia nut oil fatty acid | 3.5 |
| Alkyl silicated anhydrous silicate | 0.2 |
| Glycerin | 0.5 |
| Purified water | 1.5 |
| C. Other bases | |
| Coloring agent | q.s. |
| Perfume | q.s. |
| Antiseptic | q.s. |

(Process)

The lipstick was obtained by the same process with Compounding example 2-1.

| Compounding example 2-7 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous composition | |
| HP-β-CD | 1.0 |
| Cholesterol ester (Oleic acid) | 3.5 |
| Squalane | 2.0 |
| Alkylated polysiloxane polyethylene copolymer | 0.2 |
| Glycerin | 0.5 |
| Purified water | 1.5 |

-continued

| Compounding example 2-7 | Lipstick |
|---|---|
| C. Other bases | |
| Coloring agent | q.s. |
| Perfume | q.s. |
| Antiseptic | q.s. |

(Process)

After compounding squalane into the cholesterol ester of 60° C. for adjusting the viscosity, dispersing alkylated polysiloxane polyethylene copolymer as the hydrous stabilizer into the cholesterol ester of 60° C., and adding the solution of HP-β-CD which was dissolved into 0.5% by weight of water to it, and stirring it 10 minutes by a disper. And then, adding the rest of purified water (1.5%by weight) and glycerin to it and stirring it 10 minutes by a homomixer, and the hydrous composition was prepared. The lipstick bases were dissolved at 80° C., and the hydrous composition was added to this. And, after stirring it 10 minutes by a disper, adding coloring agent, perfume, and antiseptic to it, dispersing and stirring it. And then, forming it and the lipstick was obtained.

| Compounding example 2-8 | Cream |
|---|---|
| A. Oil phase | |
| Microcrystalline wax | 8.0 parts by weight |
| Solid paraffin | 2.0 |
| Beeswax | 3.0 |
| Petrolatum | 6.0 |
| Hydrogenated lanolin | 5.0 |
| Squalane | 30.0 |
| Hexadecyl adipate ester | 8.0 |
| Glyceryl monooleate | 3.5 |
| POE(20) sorbitol monooleate ester | 1.0 |
| B. Other bases | |
| Coloring agent | q.s. |
| Perfume | q.s. |
| Antiseptic | q.s. |
| C. Water phase | |
| Purified water | 15.0 |
| Propylene glycol | 5.0 |
| D. Hydrous composition | |
| HP-β-CD | 1.0 |
| Cholesteryl ester of macadamia nut oil fatty acid | 3.5 |
| Squalane | 2.0 |
| Alkylated polysiloxane polyethylene copolymer | 0.2 |
| Glycerin | 1.5 |
| Purified water | 1.5 |

(Process)

After compounding squalane into cholesteryl ester of macadamia nut oil fatty acid of 60° C. for adjusting the viscosity, alkylated polysiloxane polyethylene copolymer as the hydrous stabilizer was dispersed into it. Adding the solution of HP-β-CD which was dissolved into 0.5 parts by weight of purified water to it, and stirred it 10 minutes by a disper. And then, adding the rest of purified water (1.5 parts by weight) and glycerin to it and stirring it 10 minutes by a homomixer, and the hydrous composition was prepared.

After heating and dissolving the oil phase, preparing it at 70° C. by adding antiseptic agent, antioxidant, and perfume to it. Preparing by adding propylene glycol to purified water at 70° C. (water phase). The water phase was gradually added into the oil phase which was prepared in advance. After emulsifying by stirring it 10 minutes by a homomixer, adding the hydrous composition which was prepared by the above-mentioned process to it. After further stirring it 10 minutes by a homomixer, the cream was obtained by deaerating and cooling it.

(3) Hydrous composition comprising a clay mineral

Each of the compounding examples showed favorable separation stability at high temperature, and the compounding examples itself were excellent in water-holding capacity, and it became the excellent composition which had no apprehension about irritation for skin.

| Compounding example 3-1 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous composition | |
| HP-β-CD | 1.0 |
| Cholesterol ester (Isostearic acid) | 3.5 |
| Synthetic sodium magnesium silicate | 2.0 |
| Glycerin | 0.5 |
| Water | 1.0 |
| C. Other bases | |
| Coloring agent | q.s. |
| Perfume | q.s. |
| Antiseptic | q.s. |

(Process)

Dispersing alkylated polysiloxane polyethylene copolymer as the hydrous stabilizer into the cholesterol ester of 60° C., and adding the solution of HP-β-CD which was dissolved into 0.5% by weight of water to it, and stirring it 10 minutes by a disper. And then, adding the rest of water and glycerin to it and stirring it 10 minutes by a homomixer, and the hydrous composition was prepared. The hydrous composition was added to the lipstick bases which were dissolved at 80° C. And, after stirring it 10 minutes by a disper, adding coloring agent, perfume, and antiseptic to it, and dispersing and stirring it. And then, forming it and the lipstick was obtained.

| Compounding example 3-2 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous Composition | |
| HP-β-CD | 1.0 |
| Cholesterol ester (Oleic acid) | 3.5 |
| Squalane | 2.0 |
| Sodium tetra silicate mica | 0.5 |
| Glycerin | 1.0 |
| Water | 1.0 |
| C. Other bases | |
| Coloring agent | q.s. |
| Perfume | q.s. |
| Antiseptic | q.s. |

(Process)
The lipstick was obtained by the same process with Compounding example 3-1.

| Compounding example 3-3 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous composition | |
| HP-β-CD | 1.0 |
| Cholesterol ester (Oleic acid) | 3.5 |
| Squalane | 2.0 |
| Sodium tetra silicate mica | 0.5 |
| Hydrophobic silica | 0.5 |
| Glycerin | 1.0 |
| Water | 1.0 |
| C. Other bases | |
| Coloring agent | q.s. |
| Perfume | q.s. |
| Antiseptic | q.s. |

(Process)
The lipstick was obtained by the same process with Compounding example 3-1.

| Compounding example 3-4 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous composition | |
| HE-β-CD | 1.0 |
| Cholesterol ester (Oleic acid) | 3.5 |
| Sodium tetra silicate mica | 0.5 |
| Glycerin | 0.5. |
| Water | 1.5 |
| C. Other bases | |
| Coloring agent | q.s. |
| Perfume | q.s. |
| Antiseptic | q.s. |

(Process)
The lipstick was obtained by the same process with Compounding example 3-1.

| Compounding example 3-5 | Lipstick |
|---|---|
| A. Lipstick bases | |
| Carnauba wax | 0.5 parts by weight |
| Candelilla wax | 5.0 |
| Ceresin | 10.0 |
| Squalane | 30.0 |
| Glyceryl triisostearate | 10.0 |
| Glyceryl diisostearate | 20.0 |
| B. Hydrous composition | |
| HB-β-CD | 1.0 |
| Cholesteryl ester of macadamia nut oil fatty acid | 3.5 |
| Synthetic sodium magnesium silicate | 0.5 |
| Hydrophobic silica | 0.5 |
| Glycerin | 0.2 |
| Water | 2.0 |

-continued

| Compounding example 3-5 | Lipstick |
| --- | --- |
| C. Other bases | |
| Coloring agent | q.s. |
| Perfume | q.s. |
| Antiseptic | q.s. |

(Process)

The lipstick was obtained by the same process with Compounding example 3-1.

| Compounding example 3-6 | Cream |
| --- | --- |
| A. Oil phase | |
| Microcrystalline wax | 8.0 parts by weight |
| Solid paraffin | 2.0 |
| Beeswax | 3.0 |
| Petrolatum | 6.0 |
| Hydrogenated lanolin | 5.0 |
| Squalane | 30.0 |
| Hexadexyl adipate ester | 3.0 |
| Glyceryl monooleate | 3.5 |
| POE (20) sorbitol monooleate ester | 1.0 |
| B. Other bases | |
| Antiseptic | q.s. |
| Antioxidant | q.s. |
| Perfume | q.s. |
| C. Water phase | |
| Purified water | 15.0 |
| Propylene glycol | 5.0 |
| D. Hydrate composition | |
| HP-β-CD | 1.0 |
| Cholesteryl ester of macadamia nut oil fatty acid | 3.5 |
| Squalane | 2.0 |
| Synthetic sodium magnesium silicate | 0.5 |
| Glycerin | 1.5 |
| Purified water | 1.5 |

(Process)

After compounding squalane into cholesteryl ester of macadamia nut oil fatty acid of 60° C. for adjusting the viscosity, dispersing synthetic sodium magnesium silicate into it, and adding the solution of HP-β-CD which was dissolved into the purified water to it, and stirring it 10 minutes by a disper. And then, the hydrous composition was prepared.

After heating and dissolving the oil phase, preparing it at 70° C. by adding antiseptic agent, antioxidant, and perfume to it. Preparing by adding propylene glycol to water at 70° C. (water phase). The water phase was gradually added into the oil phase which was prepared in advance, after emulsifying by stirring it 10 minutes by a homomixer, adding the hydrous composition which was prepared by the above-mentioned process, to it. After further stirring it 10 minutes by a homomixer, the cream was obtained by deaerating and cooling it.

What is claimed is:

1. A cholesterol ester clathrate comprising a cholesterol ester and a hydroxyalkylated cyclodextrin.

2. A hydrous composition comprising:
   a hydroxyalkylated cyclodextrin;
   a cholesterol ester; and
   water.

3. The hydrous composition according to claim 2, wherein said cholesterol ester is partly included within said hydroxyalkylated cyclodextrin so as to form a cholesterol ester clathrate.

4. The hydrous composition according to claim 2, wherein said hydrous composition comprises:
   5 to 30% by weight of the hydroxyalkylated cyclodextrin,
   5 to 80% by weight of the cholesterol ester, and
   5 to 60% by weight of water.

Figure 1:
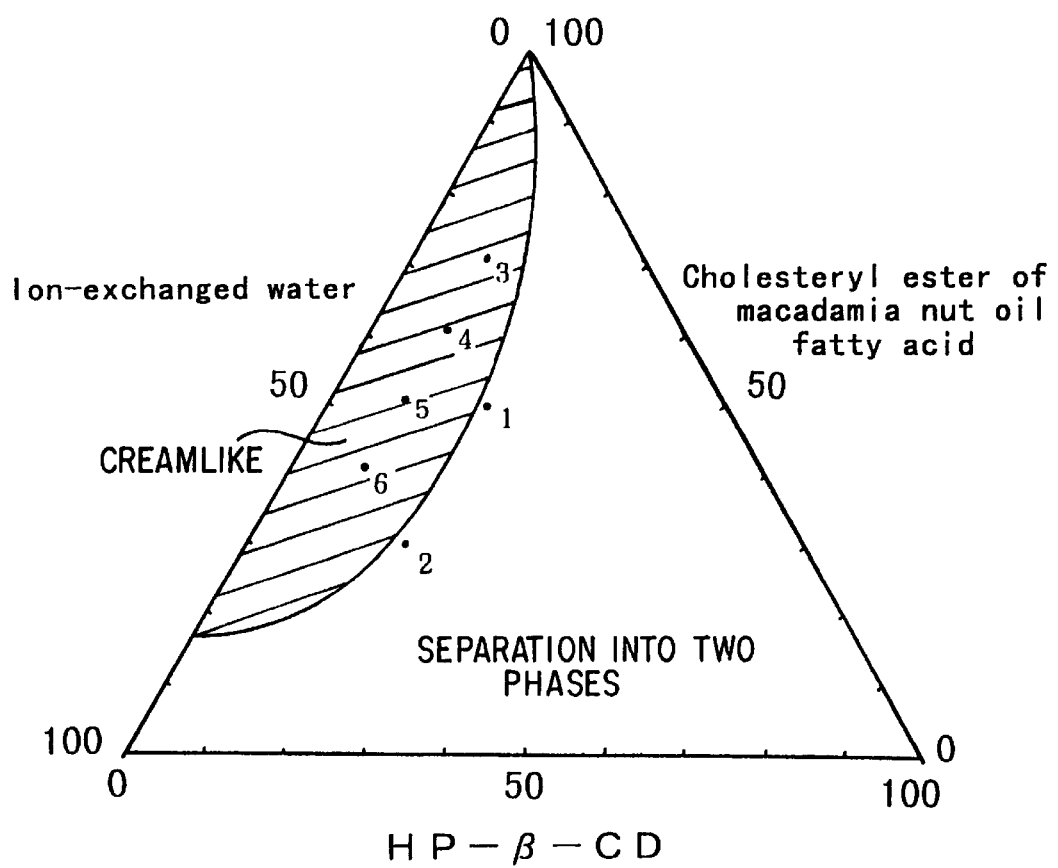
FIG. 1 is a triangular diagram which shows the ratio of the compounding amount of a HACD, a cholesterol ester and water.
Figure 2:
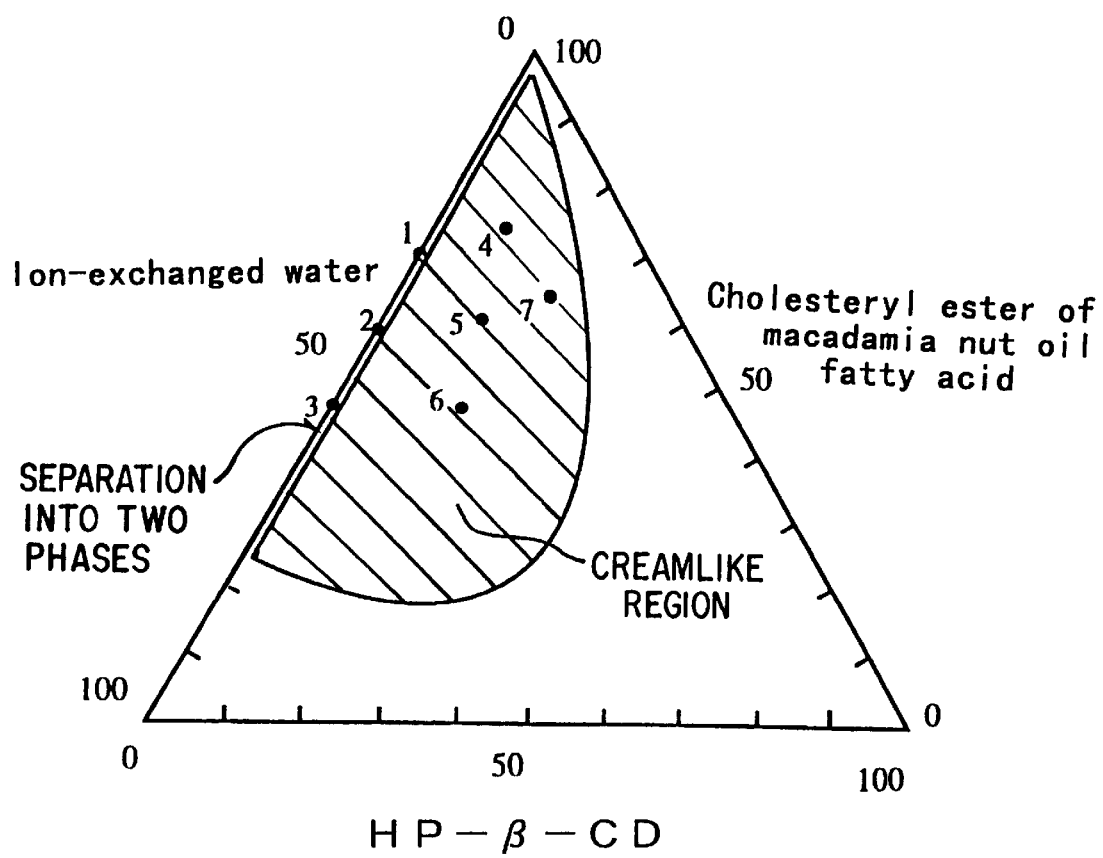
FIG. 2 is a triangular diagram which shows the ratio of the compounding amount of a HACD, a cholesterol ester, and water, in case of compounding 0.02% of a hydrous stabilizer.
Figure 3A:
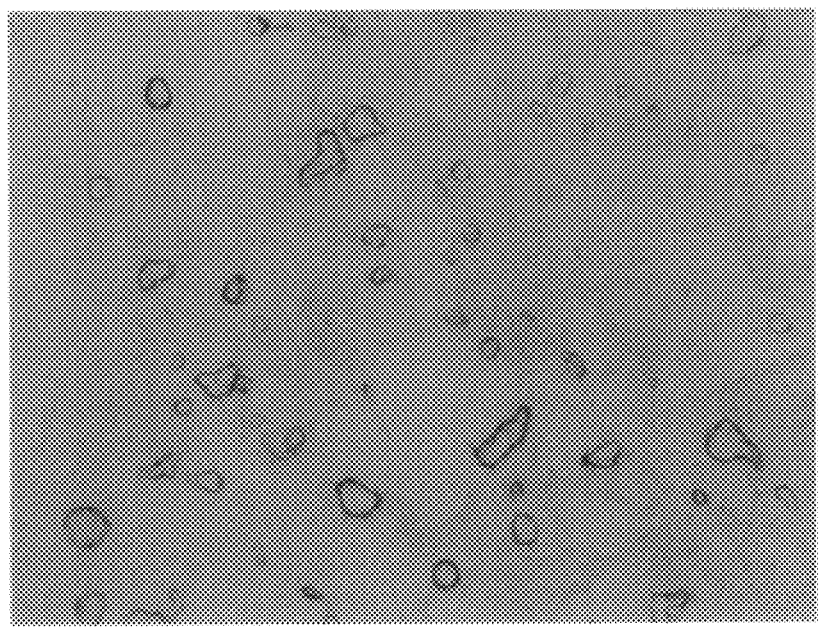
FIG. 3 are microphotographs which shows the hydration properties of Example 1-1 and Comparative example 1-1.
Figure 3B:
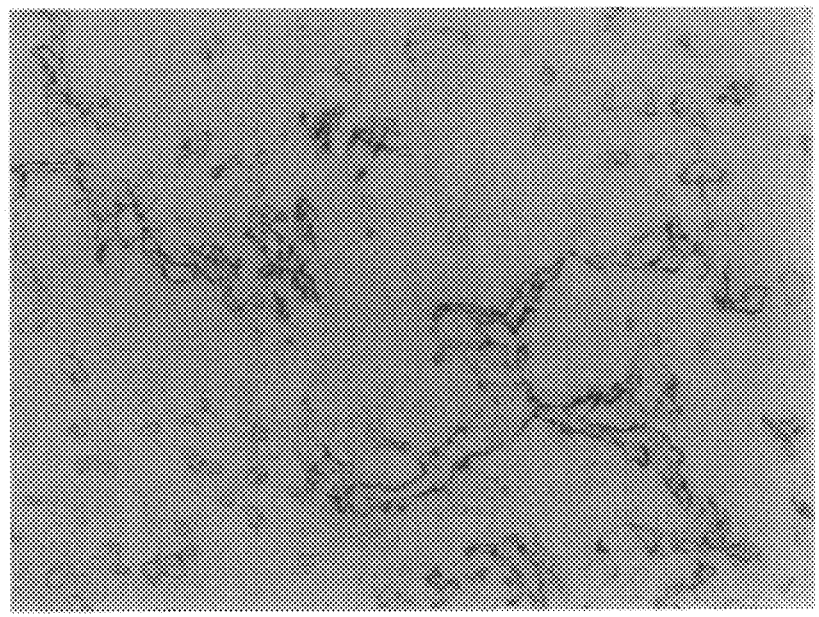
Figure 3C:
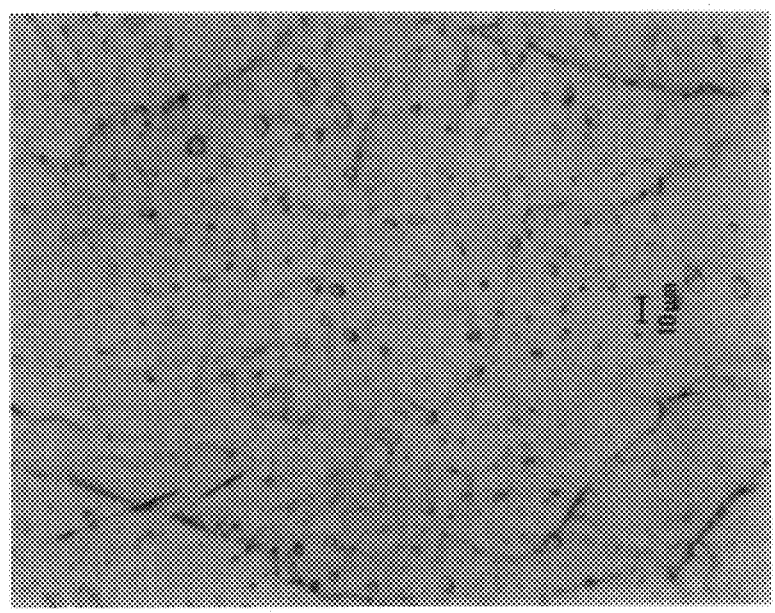
Figure 3D:
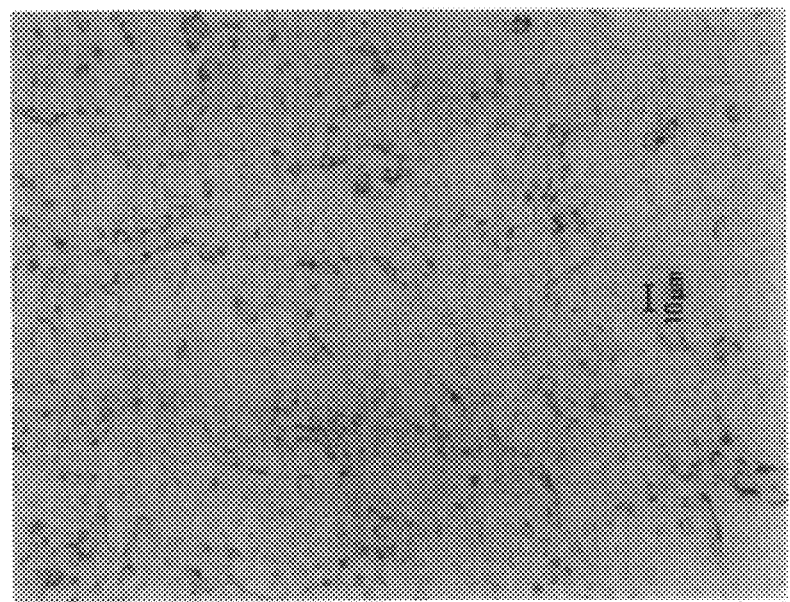

5. The hydrous composition according to claim 2, wherein relative proportions of the hydroxyalkylated cyclodextrin and the cholesterol ester are determined by coordinates along a slant line within a triangular diagram shown in FIG. 1.

6. A hydrous composition comprising:
   a hydroxyalkylated cyclodextrin;
   a cholesterol ester;
   water; and
   at least one hydrous stabilizer selected from the group consisting of alkylated polysiloxane polyethyleneglycol copolymer, alkylated silicated anhydrous silicate, alkyl-modified silicone resin coated powder, glyceryl-modified silicone resin coated powder and dextrin fatty acid ester.

7. The hydrous composition according to claim 6, wherein said composition further comprises an oily component.

8. A hydrous composition comprising:
   a hydroxyalkylated cyclodextrin;
   a cholesterol ester;
   a clay mineral; and
   water;
   and wherein said hydroxyalkylated cyclodextrin and said cholesterol ester form a cholesterol ester clathrate.

9. A hydrous composition according to claim 8, wherein the clay mineral is either a swelling clay mineral or an organophilic smectite.

10. The hydrous composition according to claim 8, wherein the clay mineral is a synthetic sodium magnesium silicate.

11. The hydrous composition according to claim 8, wherein said hydrous composition further comprises a hydrophobic silica.

12. A cosmetic comprising a composition comprised of:
    a hydroxyalkylated cyclodextrin;
    a cholesterol ester; and
    water;
    and wherein said hydroxyalkylated cyclodextrin and said cholesterol ester form a cholesterol ester clathrate.

13. The cosmetic according to claim 12, wherein the composition is a water-in-oil composition.

14. The cosmetic according to claim 12, wherein the composition is a hydrous composition compounded in an amount from 0.5 to 30% by weight with respect to the whole amount of the cosmetic.

15. A process for the preparation of a cholesterol ester clathrate comprising the steps of:
    mixing and stirring a cholesterol ester with a hydroxyalkylated cyclodextrin to form said cholesterol ester clathrate.

16. A process for the preparation of a hydrous composition comprising the steps of:
    stirring and mixing a hydroxyalkylated cyclodextrin with a cholesterol ester to form a cholesterol ester clathrate; and
    adding water to said cholesterol ester clathrate to form said hydrous composition.

17. A process for the preparation of a hydrous composition comprising the steps of:

stirring and mixing a cholesterol ester, a hydroxyalkylated cyclodextrin and water to form said hydrous composition.

18. The process for the preparation of a hydrous composition according to claim 16, wherein the hydroxyalkylated cyclodextrin is 5 to 30% by weight, said cholesterol ester is 5 to 80% by weight, and said water is 5 to 60% by weight, with respect to the whole amount of the hydrous composition.

19. The process for the preparation of a hydrous composition according to claim 17, wherein the hydroxyalkylated cyclodextrin is 5 to 30% by weight, said cholesterol ester is 5 to 80% by weight, and said water is 5 to 60% by weight, with respect to the whole amount of the hydrous composition.

20. The process for the preparation of a hydrous composition according to claim 16, wherein the relative proportions of the hydroxyalkylated cyclodextrin and the cholesterol ester are determined by coordinates along the slant line of the triangular diagram shown in FIG. 1.

21. The process for the preparation of a hydrous composition according to claim 17, wherein the relative proportions are determined by coordinates along the slant line of the triangular diagram shown in FIG. 1.

22. A process for the preparation of a hydrous composition comprising the steps of:

stirring and mixing a hydroxyalkylated cyclodextrin with water and at least one hydrous stabilizer, wherein said hydrous stabilizer is selected from the group consisting of alkylated polysiloxane polyethyleneglycol copolymer, alkylated silicated anhydrous silicate, alkyl-modified silicone resin coated powder, glyceryl-modified silicone resin coated powder and dextrin fatty acid ester; and admixing a cholesterol ester.

23. The process for the preparation of a hydrous composition according to claim 22, further comprising the step of adding an oily component.

24. A process for the preparation of a hydrous composition comprising the steps of:

mixing and stirring a hydroxyalkylated cyclodextrin, a cholesterol ester, a clay mineral and water.

25. The process for the preparation of a hydrous composition according to claim 24, wherein the clay mineral is either a swelling clay mineral or an organophilic smectite.

26. The process for the preparation of a hydrous composition according to claim 24, further comprising the steps of:

mixing and stirring said hydrous composition with a hydrophobic silica.

27. The process for the preparation of the hydrous composition according to claim 26, wherein the hydrophobic silica is compounded in an amount from 0.01 to 20% by weight.

28. A process for the preparation of a cosmetic comprising the steps of:

stirring and mixing a hydrous composition of claim 12 with cosmetic ingredients.

29. The process for the preparation of a cosmetic according to claim 28, wherein said hydrous composition is compounded in an amount from 0.5 to 30% by weight of the whole amount of the cosmetics.

30. The process for the preparation of a cosmetic according to claim 28, wherein said cosmetic ingredients are selected from the group consisting of macadamia nut oil, evening primrose oil, castor oil, olive oil, mink oil, jojoba oil, lanolin, squalene, liquid paraffin, paraffin wax, polyethylene wax, carnauba wax, cetyl alcohol, isocetyl alcohol, stearyl alcohol, isostearyl alcohol, myristic acid, palmitate, stearate, behenic acid, isostearate, isopropyl myristate, isopropyl palmitate, isopropyl isostearate, diisostearyl malate, trimethylolpropane triisostearate, glyceryl isostearate, neopentyl glycol dicaprate, glyceryl 2-ethylhexanoate, diethylene glycol monopropylene pentaerythritol ether, ethyl linoleate, polyoxypropylene butyl ether, silicone oils, D-mannitol, lactose, glycerin, hyaluronic acid, vitamin C, vitamin E, perfume, and pigment.

31. The hydrous composition according to claim 2 wherein wherein said hydroxyalkylated cyclodextrin and said cholesterol ester form a cholesterol ester clathrate.

32. The hydrous composition according to claim 3, wherein said composition further comprises at least one hydrous stabilizer selected from the group consisting of alkylated polysiloxane polyethyleneglycol copolymer, alkylated silicated anhydrous silicate, alkyl-modified silicone resin coated powder, glyceryl-modified silicone resin coated powder and dextrin fatty acid ester.

* * * * *